United States Patent
Timmerman

(10) Patent No.: US 7,651,842 B2
(45) Date of Patent: Jan. 26, 2010

(54) IMUNOGENIC COMPLEX COMPRISING RIBOSOMES

(75) Inventor: Benedikt Timmerman, Toulouse (FR)

(73) Assignee: BT Pharma, Labege (FR)

( * ) Notice: Subject to any disclaimer, the term of this patent is extended or adjusted under 35 U.S.C. 154(b) by 516 days.

(21) Appl. No.: 10/250,664

(22) PCT Filed: Jan. 4, 2002

(86) PCT No.: PCT/IB02/00739

§ 371 (c)(1),
(2), (4) Date: Jul. 7, 2003

(87) PCT Pub. No.: WO02/053178

PCT Pub. Date: Jul. 11, 2002

(65) Prior Publication Data

US 2004/0115210 A1    Jun. 17, 2004

(30) Foreign Application Priority Data

Jan. 6, 2001    (GB)  ................................. 0100757.4

(51) Int. Cl.
*G01N 33/53* (2006.01)
*C12Q 1/70* (2006.01)
(52) U.S. Cl. .......................... 435/7.1; 435/5; 435/7.31
(58) Field of Classification Search ................ 435/7.1; 424/197.1
See application file for complete search history.

(56) References Cited

U.S. PATENT DOCUMENTS 4,460,575 A * 7/1984 d'Hinterland et al. .. 424/197.11
2004/0234536 A1* 11/2004 Bhatia et al. ............. 424/184.1

FOREIGN PATENT DOCUMENTS

| EP | 0 238 407 A1 | 9/1987 |
| FR | 2 790 961 A1 | 9/2000 |
| WO | WO 00/24773 A2 | 5/2000 |
| WO | WO 00/54790 A1 | 9/2000 |
| WO | WO 02/40717 | * 5/2002 |

OTHER PUBLICATIONS

Fayolle et al. (The Journal of Immunology vol. 162, pp. 4157-4162, 1999).*
Bernkop-Schnurch et al. (Journal of Pharmaceutical Sciences, vol. 87, No. 4, Apr. 1998).*
Staab et al. (Science, vol. 283, Mar. 1999).*
Gaur et al. (Infection and Immunity, vol. 65, No. 12, pp. 5289-5294, Dec. 1997).*
Burgess et al. (J of Cell Biology, 1990 vol. 111, pp. 2129 2138) t.*
Lazar et al (Molecular and Cellular Biology, 1988, vol. 8, pp. 1247 1252).*
Ellis, R.W. (Chapter 29 of "Vaccines" [Plotkin, S.A. et al. (eds) published by W.B. Saunders company (Philadelphia) in 1988.*
Schultze et al (Trends in Immunology, 2004, vol. 25, pp. 659-664).*
Bodey et al, (Anticancer Research, 2000, vol. 20, pp. 2665-2676).*
Brand et al., "Crystalline Antigen from the Influenze Virus Envelope," Nature New Biology, Aug. 2, 1972, 238:145-147.
Cox et al., "Experimental Induction of Diarrhoea in Newly-Weaned Piglets," J. Vet. Med., 1991, 38:418-426.
Gietz et al., "Transforming Yeast with DNA," Methods in Molecular and Cellular Biology, 1995, 5:255-269.
Gregory et al., "Effective Immunity to Dental Caries: Protection of Gnotobiotic Rats by Local Immunization with a Ribosomal Preparation from *Streptococcus mutans*," Microbiol. Immunol., 1983, 27(9):787-800.
Hoffman et al., "A ten-minute DNA preparation from yeast efficiently releases autonomous plasmids for transformation of *Escherichia coli*," Gene, 1987, 5:267-272.
Jacobs et al., "Production of K88, K99 and F41 fibrillae in relation to growth phase, and a rapid procedure for adhesin purification," FEMS Microbiology Letters, 1985, 26:15-19.
Papaoiannou et al., "Bacterial adhesion on Mono- and on Multi-Layers of Pocket Epithelium," J. Periodontol., Jun. 1999, 70(6):622-625.
Yusupov et al., "Hot Tritium Bombardment Technique for Ribosome Surface Topography," Methods in Enzymology, 1988, 164:426-439.
Ross et al., The secreted aspartate proteinase of *Candida albicans*: physiology of secretion and virulence of a proteinase-deficient mutant, Journal of General Microbiology, 1990, 136:687-694.
Papaioannou et al., "Comparison of Fluorescnece Microscopy and Culture Assays to Quantitate Adhesion of *Porphyromonas gingivalis* to Mono- and Multi-Layered Pocket Epithelium Cultures," J. Periodontal., Jun. 1999, 70(6):618-625.
Silhavy, T.J., "Procedure 25, DNA Extraction from Bacterial Cells," Experiments with Gene Fusions, 1984, 137-139.
Staehelin et al., "On the Catalytic Center of Peptidyl Transfer: A Part of the 50 S Ribosome Structure," Cold Spring Harbour Symposia on Quantitative Biology, 1969, 34:39-48.

* cited by examiner

*Primary Examiner*—Robert Mondesi
*Assistant Examiner*—Khatol Shahnan-Shah
(74) *Attorney, Agent, or Firm*—Foley & Lardner LLP

(57) ABSTRACT

The present invention relates to an Immunogenic Complex comprising Ribosomal Complex and Adhesion of a Microbe or Ribosomal Complex and a viral antigen. The Ribosomal Complex is composed of the subunits of ribosomes (50 S and 30 S subunits in bacteria and 60 S and 40 S subunits of eucaryotes), the ribosomal subunits generally retaining sufficient integrity to preserve substantially the double-stranded nature of the large r-RNA's (16 S and 23 S in bacteria; 18 S and 28 S in eukaryotic cytosol) contained in the ribosomal subunits.

42 Claims, No Drawings

IMUNOGENIC COMPLEX COMPRISING RIBOSOMES

FIELD OF THE INVENTION

This invention relates to a prophylactic and therapeutic Immunogenic Complex, method of preparation thereof and pharmaceutical compositions containing the same.

BACKGROUND OF THE INVENTION

The broad and intense use of anti-microbial agents in medical and veterinary care is accelerating the rate at which the target Microbes are developing resistance. Alternative approaches are needed to complement the use of antibiotics in disease treatment. Vaccines constitute such an alternative by allowing our immune system early detection and elimination of pathogens.

The immune system has different, complementary and super-imposed components such as innate anti-microbial molecules, the Complement System, the Humoral and Cellular responses. Humoral immunity relies on antibody production. Immuno-globulins or antibodies are proteins which are the effectors of humoral immunity: they are secreted by so-called B lymphocytes in response to antigen, are released into the body fluids where they directly recognize the antigen to which they were designed to bind. Cellular immunity is mediated by cytotoxic T lymphocytes (CTL) which respond to degraded (peptide) fragments of antigens which appear on the surface of the target cell bound to proteins called class I major histo-compatibility complex (MHC) molecules. Virtually all nucleated cells have MHC I molecules on their surface. Apparently upon turn-over of proteins in the cell, peptide fragments bind to the MHC molecules and are transported to the cell surface hereby marking the cell as "self" i.e. belonging the host. For a foreign antigen of a pathogen, that enters the body, to elicit an immune response, it needs to be recognized by the immune system where it can activate specific B cells by binding to surface immuno-globulins and also needs to be taken up by specialized lymphoid cells that process the antigen and export the fragments to the cell surface in association with a different series of MHC molecules: class II MHC's. Peptides bound to class II molecules are presented to helper T cells which become activated and secrete cytokines such as Inter-leucine 2 (IL-2). Depending on still incompletely understood factors the activated Helper T cells lead, on the one hand to the production of Memory B cells and Ig-secreting plasma cells; on the other hand these Helper T cells can induce proliferation of cytotoxic T lymphocytes. CTL's recognize host cells infected by the pathogen and destroy those cells.

Despite the tremendous positive effect of vaccination on global health care, its potential is far from exploited as for many diseases the use of attenuated or inactivated pathogens as antigen sources has stumbled on production, safety and efficacy issues. Synthetic peptide (subunit) vaccines, based on peptide antigens of pathogens rather than on the entire organism, circumvent most of the weaknesses of attenuated or inactivated pathogen vaccines but have often encountered disappointing results because of different reasons: the peptides may not readily associate with MHC molecules, may have a short serum half-life, or are proteolyses or otherwise cleared before being exposed to antigen-presenting macrophages and monocytes. Today's relatively poor understanding of the parameters required for the engineering of safe but highly immunogenic antigens are the reasons for the continued empirical approach to vaccine development.

The invention provides a novel immunogenic complex offering new possibilities for prophylactic and therapeutic control of microbial pathogens. The Immune Complex comprises specific preparations of ribosomes of micro-organisms (as defined below) and specific microbial cell surface proteins, called adhesins (as defined below). The immunogenic complex of this invention targets mainly the Mucosal Immune System. The Mucosal Immune System is found in the gastrointestinal, uro-genital, and respiratory tract of animals and humans. These tissues are covered with a mucosal surface, mostly covered with a single layer of epithelial cells and under which the mucosal immune tissues lie. The Organized Mucosal-Associated Lymphoid Tissue or O-MALT constitutes the specialized inductive sites of the mucosal immune system; the Diffuse mucosal-Associated Lymphoid Tissue or D-MALT constitutes the dispersed effector sites. Both the O-MALT and D-MALT are separated from mucosal surface antigens by epithelial barriers. The O-MALT, where an immune response is initiated, consists of solitary and aggregated lymphoid follicles underlying the mucosal surfaces. Aggregated lymphoid follicles occur mostly in the naso-pharyngeal tonsils and adenoids and are known as Peyer's patches in the small intestine and equivalent structures in the appendix. Single lymphoid follicles are found along the bronchus and the entire gastrointestinal tract.

Youmans and Youmans proposed the use of ribosome extracts as protective vaccines (Youmans A. S. and Youmans G. P., 1965). Since then experimental vaccines incorporating ribosomal preparations from different bacterial, fungal and protozoan microorganisms have been described. Few of these vaccines have made it beyond the laboratory experiment, probably because the active principles of ribosomal extracts were commonly lost upon preparation, leading to irregular and even contradictory results.

Most classic vaccines are injected and mainly lead to the induction of systemic IgG-type antibodies. The immunogenic complex described here, targets mainly the mucosal immune system and leads to the production of high levels of secreted IgA's besides IgG's. Advantages of delivery to and induction of the mucosal immune system are that injection and its intrinsic dangers are avoided and that the Mucosal Immune System has been shown to be less affected by immune depressing agents such as HIV, chemio- or radiotherapy and is earlier and stronger activated in babies and small children.

SUMMARY OF THE INVENTION

The invention provides an immunogenic complex containing at least ribosomal complex and proteineous adhesins of microbes. The unique and deliberate combination of both elements of the immunogenic complex is surprisingly superior in immune induction and immune protection against the target microbial pathogen than either component alone and constitutes active ingredients of superior prophylactic or therapeutic vaccines.

The Immunogenic Complex can be used as a prophylactic vaccine to prevent establishment of diseases but can also be used as a therapeutic agent thanks to its immune-stimulatory effect and effective antigen presenting capability and consequently complements the natural defense against disease. Methods of use, manufacture and administration of pharmaceutical compositions containing above mentioned immunogenic complex are also described.

The present invention thus provides an Immunogenic Complex comprising at least one Ribosomal Complex and (a) at least one Adhesin of a Microbe; or (b) at least one antigen of a virus. Preferably, the Ribosomal Complex is composed of the large and small subunits of ribosomes which are particulate in nature, and/or carries minor fractions of the microbial cellular membrane or cell wall—components. Preferably, the Ribosomal Complex retains sufficient integrity to substantially preserve the double-stranded nature of the large r-RNA's contained in the subunits of ribosomes.

Preferably, an Adhesin is any protein embedded in or on the surface of any Microbe, which protein is involved in the attachment of the Microbe to the host cell surface, optionally any protein structurally similar to, or any polypeptide derived from or corresponding to part of any protein embedded in or on the surface of a Microbe which can still induce an antibody response to said protein. The host cells are typically eukaryotic cells belonging to vertebrate animal groups aves, Pisces and mammalia, including humans, most preferably absorptive enterocytes, M-cells, dendritic cells, macrophages, erythrocytes, fibroblasts and / or epithelial cells.

Preferably, an Immunogenic Complex of the invention comprises Adhesin that binds to components of the extracellular matrix that embed host cells. Preferred extracellular matrix components are selected from fibronectin, laminin, collagen, fibrogen, vitronectin or heparin sulfate or analogues, homologues or derivatives of these. In preferred examples, the Adhesin is a protein included in colonization factor antigens present in bacterial fimbriae, or a protein included in colonization factor antigens present in fungal hyphae. Also encompassed is an Immunogenic Complex as descroned comprising Ribosomal Complex and Adhesin which originate from multiple Microbe species, wherein Microbe species is any species belonging to bacteria and/or fungi and/or protozoae. Provided also is an Immunogenic Complex of the invention, where the Ribosomal Complex and Adhesin which originate from multiple Microbe species, whereby from one or more species of Microbes, only Ribosomal Complex but not Adhesin or only Adhesin and not Ribosomal Complex, is included (herein called Heterologous Immunogenic Complex). According to the embodiments of the invention, Ribosomal Complex and/or Adhesin preferably originate from a microbe selected from the group consisting of: *Actinobacillus actinomycetemcomitans*; Bacille Calmette-Guérin; *Blastomyces dermatitidis; Bordetella pertussis; Campylobacter consisus; Campylobacter recta; Candida albicans; Capnocytophaga* sp.; *Chlamydia trachomatis; Eikenella corrodens; Entamoeba histolitica; Enterococcus* sp.; *Escherichia coli; Eubacterium* sp.; *Haemophilus influenzae; Lactobacillus acidophilus; Leishmania* sp.; *Listeria monocytogenes; Mycobacterium vaccae; Neisseria gonorrhoeae; Neisseria meningitidis; Nocardia* sp.; *Pasteurella multocida; Plasmodium falciparum; Porphyromonas gingivalis; Prevotella intermedia; Pseudomonas aeruginosa; Rothia dentocarius; Salmonella typhi; Salmonella typhimurium; Serratia marcescens; Shigella dysenteriae; Streptococcus mutants; Streptococcus pneumoniae; Streptococcus pyogenes; Treponema denticola; Trypanosoma cruzi; Vibrio cholera*; and *Yersinia enterocolitica*.

In further aspects, the invention comprises a Bacterio-viral Immunogenic Complex according to the invention, characterized in that viral antigen originates from a virus selected from the group consisting of: Influenza virus; parainfluenza virus; rhinovirus; hepatitis A virus; hepatitis B virus; hepatitis C virus; apthovirus; coxsackievirus; Rubella virus; rotavirus; Denque virus; yellow fever virus; Japanese encephalitis virus; infectious bronchitis virus; Porcine transmissible gastroenteric virus; respiratory syncytial virus; Human immunodeficiency virus; papillomavirus; Herpes simplex virus; varicellovirus; Cytomegalovirus; variolavirus; Vacciniavirus; and suipoxvirus. In a preferred Immunogenic Complex according to the invention, Ribosomal Complex and Adhesin or viral antigen are present in weight ratios respectively from 1 to 20 and 20 to 1.

Preferably, the Ribosomal complex and Adhesin or viral antigen are incorporated in a polymeric matrix, for example a matrix comprising or consisting of chitosan-EDTA Bowman-Birk Inhibitor conjugate. In other embodiments, the Ribosomal complex and Adhesin or viral antigen are incorporated in microparticles. In other embodiments of the Immunogenic Complex according to the invention, Ribosomal Complex and Adhesin or viral antigen which are non-covalently bound to each other by ionic interactions, or are covalently coupled. Coupling can be chemically achieved using N-hydroxysuccinimidyl esters, bis-imido esters or preferably 1-(3-dimethylaminopropyl)-3-ethylcarbodiimide (EDC) or glutaraldehyde.

Also encompassed by the present invention are Pharmaceutical Composition for prevention and treatment of infectious disease caused by Microbe or virus, comprising Immunogenic Complex according to the invention, wherein the Immunogenic Complex is formulated as a pharmaceutically acceptable delivery form for administration to animals and/or humans. Pharmaceutical composition according to the invention can be used as prophylactic vaccine against a Microbe or a virus, in particular a Microbe as described herein. Preferably an immune response is activated against antigens, including Adhesins, expressed by the Microbes during their established pathogenic phase.

Embodiments according to the invention include Pharmaceutical composition to prevent or control disease caused by toxigenic *E. coli*, wherein Ribosomal Complex is derived from *E. coli* and includes as Adhesin, Fae G fimbrial protein, or proteins structurally similar to, or any polypeptide derived from or corresponding to part of Fae G protein, which can still induce an antibody response to Fae G.

Also embodied are Pharmaceutical composition to prevent or control Candida infection, wherein Ribosomal Complex is derived from *Candida albicans* and includes as Adhesin, ALA1 of *C. albicans* or a protein structurally similar to, or any polypeptide derived from ALA1, or corresponding to part of the Ala1 gene product, which can still induce an antibody response to ALA1.

Included also in the invention are Pharmaceutical composition to prevent or control Candida infection, wherein Ribosomal Complex is derived from *Candida albicans* and includes as Adhesin, the HWP1 protein of *C. albicans* or a protein structurally similar to, or any polypeptide derived from HWP1 or corresponding to part of the hwp1 gene product, which can still induce an antibody response to HWP1.

Included also is a Pharmaceutical composition to prevent or control periodontal disease associated with colonization or infection by *Porphyromonas gingivalis*, wherein the Ribosomal Complex is derived from *P. gingivalis*; or a Pharmaceutical composition to prevent or control periodontal disease associated with colonization or infection by *Porphyromonas gingivalis* and/or *Treponema denticola*, wherein Ribosomal Complex is derived from *P. gingivalis* and *T. denticola* and includes as Adhesin, the Msp protein of *T. denticola*, or a protein structurally similar to, or any polypeptide derived from Msp or corresponding to part of msp gene product, which can still induce an antibody response to Msp. Embodied also is a Pharmaceutical composition to prevent or control periodontal disease associated with colonization or infection by *Porphyromonas gingivalis* and/or *Campylobacter rectus* and/or *Treponema denticola*, wherein Ribosomal Complex is derived from *P. gingivalis, C. rectus* and *T. denticola* and includes as Adhesin, the Msp protein of *T. denticola*, or a protein structurally similar to Msp, or any polypeptide derived from or corresponding to part of msp gene product, which can still induce an antibody response to Msp.

The Immunogenic Complex or the pharmaceutical composition can be used in the preparation of a medicament for prophylaxis or treatment of infectious diseases in humans or in animals, or for prophylaxis or treatment of toxigenic *E. coli* infection, for prophylaxis or treatment of Candida infection, for prophylaxis or treatment of periodontal disease, for prophylaxis or treatment of respiratory diseases in humans or in animals, for prophylaxis or treatment of diseases caused by respiratory syncytial virus in humans or in animals, or for prophylaxis or treatment of periodontal disease caused or aggravated by any one of following bacteria: *Porphyromonas gingivalis, Campylobacter rectus, Treponema denticola*.

Also encompassed is therefore a method of treating infectious diseases in humans or animals, or of providing prophylaxis in respect to said diseases, comprising administrating to said humans or animals an effective amount of the Immunogenic Complex or of the pharmaceutical composition of the invention. Preferably the method is for the treatment or prophylaxis of diseases caused by toxigenic *E. coli* infection, caused by Candida infection, caused or aggravated by periodontal bacteria, or caused or aggravated by any one of following bacteria: *Porphyromonas gingivalis, Campylobacter rectus, Treponema denticola*; or caused or aggravated by respiratory syncytial virus.

Also included in this invention are methods for the manufacture of the Immunogenic Complex of the invention comprising admixing Ribosomal Complex and Adhesin of one or multiple Microbes. Preferably the Ribosomal Complex and Adhesin are incorporated in a polymeric matrix containing chitosan-EDTA Bowman-Birk Inhibitor conjugate, or are incorporated in microparticles containing carboxymethylethylcellulose-coated poly[dl-lactide-co-glycolide]. In other methods, the Ribosomal Complex and Adhesin are non-covalently bound to each other by ionic interaction, or are covalently coupled to each other. Coupling can be achieved preferably using N-hydroxysuccinimidyl esters like disuccinimidyl suberate or N-succinimidyl-(3-[2-pyridyl]-dithio) propionate (SPDP), 1-(3-dimethylaminopropyl)-3-ethylcarbodiimide (EDC), bis-imido esters such as dimethyladipimidate or glutaraldehyde. The pharmaceutical composition may also involve admixing a pharmaceutically acceptable carrier, diluent or other excipient.

Also envisioned are methods of administration of the Immunogenic Complex or the pharmaceutical composition according to the invention to humans and/or animals. Examples include oral administration of the Immunogenic Complex or the pharmaceutical composition upon suspension in a drinkable liquid, Topical administration of the Immunogenic Complex or the pharmaceutical composition contained in a liquid, a gel or cream and applied to epithelial cell surfaces, in particular to surfaces of infected or infection-prone areas, nasal administration of the Immunogenic Complex or the pharmaceutical composition contained in a liquid aerosol or droplet dispenser, by inhalation upon containment in a peroral liquid or dry powder aerosol, and Rectal or vaginal or uteral application of the Immunogenic Complex or the pharmaceutical composition contained in a suppository or as a gel or cream.

DETAILED DESCRIPTION OF THE INVENTION

The present invention pertains to immunogenic complexes, the production and formulation thereof, methods of application and the use of immunogenic complexes as either prophylactic vaccines or therapeutic agents in Pharmaceutical compositions. It will be readily apparent to one skilled in the art that various substitutions and modifications may be made to the invention disclosed herein without departing from the scope and spirit of the invention.

As used herein, the term "Microbes" refers to bacteria, protozoa and fungi.

As used herein, the term "Ribosomal Complex" refers to a complex which is essentially composed of the subunits of ribosomes (50 S and 30 S subunits in bacteria and 60 S and 40 S subunits in eucaryotes) which carry on their surface minor fractions of the microbial cellular membrane or cell wall components.

An important feature of the invention is that the ribosomal subunits in the Ribosomal Complex retain sufficient integrity to preserve substantially the double-stranded nature of the large r-RNA's (16 S and 23 S in bacteria; 18S and 28S in eukaryotic cytosol) contained in the ribosomal subunits.

The Ribosomal Complex is largely particulate in nature. This granular (versus soluble) structure is another important feature of Ribosomal Complex, which plays a role in efficient uptake of the Ribosomal Complex by lymphoid cells such as M cells and Dendritic cells. The effect of Ribosomal Complex is to function as a carrier for additional antigens, to ensure effective endocytosis of the Immunogenic Complex by host lymphoid cells such as M-cells or Dendritic cells at inductive sites of the immune system and to produce an adjuvant effect which boosts the immune response.

As used herein, the term "Adhesin" refers to any protein embedded in or on the surface of Microbes that is involved in the attachment to host cells such as absorptive enterocytes, M-cells, dendritic cells, macrophages, erythrocytes, fibroblasts and epithelial cells or in binding to components of the extra-cellular matrix that embeds host cells such as fibronectin, laminin, collagen, fibrogen, vitronectin, heparin sulfate. "Adhesin" also includes any polypeptide derived from or corresponding to part of such protein that can still induce an immune response against said Adhesin. "Adhesin" also includes the protein complexes of colonization factor antigens such as those present in bacterial fimbriae and fungal hyphae.

The effect of including Adhesin in the immunogenic complex is to enhance the immune response specifically against said adhesins and further contribute to effective immune exclusion of the target micro-organisms antibody-mediated or cellular immune responses. Microbes may express multiple Adhesins on their surface and recognize a variety of host extra-cellular matrix proteins or host cell types.

As used herein, the term "Immunogenic Complex" refers to a complex containing at least following elements: Ribosomal Complex and Adhesin of a Microbe.

An Immunogenic Complex can contain Ribosomal Complex and Adhesins of several species of Microbes. This is particularly advantageous for disease prevention and/or treatment of diseases, which may be caused or aggravated by multiple pathogens (e.g. periodontal disease), or by sequential pathogens (e.g. common cold, angina, bronchitis).

As used herein, the term "Heterologous Immunogenic Complex" refers to an Immunogenic Complex comprising Ribosomal Complex and Adhesin which originate from different, or multiple Microbes, whereby from one or more species of Microbes, only Ribosomal Complex but not Adhesin or only Adhesin and not Ribosomal Complex, is included.

This is particularly advantageous in cases where an immune response is desirable against a given pathogen in a complex of Microbes against which one wishes to use the Heterologous Immunogenic Complex but for which pathogen the use of both Ribosomal Complex and Adhesin is not desirable, and it is preferable to include only Ribosomal Complex or only Adhesin of this Microbe. Concerning Adhesins, this could be the case when, for example, the Adhesin is not or poorly characterized (e.g. *Campylobacter rectus*) or are difficult or expensive to isolate without loss of their immunogenicity, or induce an immune response which cross-reacts with host tissue. Concerning Ribosomal Complex, examples where it may be desirable to leave this component out for a certain Microbe against which one wishes to produce an immune response, are in cases where the Microbe is difficult or expensive to produce in large quantities (e.g. many oral treponemes associated with periodontal problems); another obvious reason is where an immune response is induced which cross-reacts with host tissue (observed with *Streptococcus pyogenes A*).

As used herein, the term "Bacterio-viral Immunogenic Complex" refers to an Immunogenic Complex, containing at least following elements: Ribosomal Complex of bacteria and an Antigen of virus.

Similarly to Immunogenic Complex, the Bacterio-viral Immunogenic Complex is advantageous for disease prevention and/or treatment of diseases resulting from infection by several pathogens. In particular are concerned diseases which may initiate as result of viral infection which facilitate colonisation of bacterial pathogens, that super-infect and aggravate and prolong the disease (e.g. Common Cold, Broncheolitis, diarrhoea's, Meningitis caused by Neisseria meningitis following infection by respiratory syncytial virus, etc.).

As used herein, the term "antigen" refers to any macromolecule including protein, glyco-protein, polypeptide, polysaccharide, lipo-polysaccharide, that is able to interact specifically with an Antigen recognition molecule of the immune system, such as an antibody (immunoglobulin) or T cell-antigen receptor. An antigenic portion of a molecule can be the portion that is immuno-dominant for antibody or T cell receptor recognition, or it can be a portion of such protein, which when fused to a carrier molecule for immunization, is capable of inducing specific Antigen recognition molecules that will bind to it. A molecule that is antigenic need not be itself immunogenic, i.e., capable of eliciting an immune response without a carrier molecule.

The phrase "pharmaceutically acceptable" refers to molecular entities and compositions that are physiologically tolerable and do not typically produce an allergic or similar undesirable reaction, such as gastric upset, dizziness, fever and the like, when administrated to a human. Preferably, as used herein, the term "pharmaceutically acceptable" means fulfilling the guidelines and approval criteria of a European Community country's Drug Registration Agency concerning products to be used as a drug, or means that the pharmaceutically acceptable compound, composition, method or use, is listed in the European Community country's Pharmacopoeia or other generally recognized pharmacopoeia for use in animals, and more particularly in humans.

The term "pharmaceutical carrier" refers to a diluent, adjuvant, excipient, or vehicle with which the compound is administered. Such pharmaceutical carriers include but are not limited to sterile liquids, such as water and oils, including those of petroleum, oil of animal-, vegetable-, or synthetic origin, such as whale oil, sesame oil, soybean oil, mineral oil and the like. Water or, aqueous solutions, saline solutions, and aqueous dextrose and glycerol solutions are preferably employed as carriers, particularly for injectable solutions, droplet-dispensed solutions and aerosols.

The term "adjuvant" refers to a compound or mixture that enhances the immune response to an antigen. An adjuvant can serve as a tissue depot that slowly releases the antigen and also as a lymphoid system activator that non-specifically enhances the immune response Preferably, the adjuvant is pharmaceutically acceptable.

Protocols describing the preparation of Ribosomal Complex (RC) from Microbes are available in the literature and can be adapted where needed by those skilled in the art. For example, the preparation of RC from bacteria can be done essentially as described by Youmans and Youmans, 1965 and adapted as described by Gregory et al., 1983. Briefly, in the case of RC preparation from bacteria, the bacterial culture is grown in regular broth at a temperature and atmospheric conditions optimal for the species. Subsequently the cells, whilst still in log phase growth, are rapidly cooled to 10° C., harvested by low-speed centrifugation (10.000×g for 10 min.), washed three times in a phosphate buffer (0.01M, pH 7.0) containing 0.01 M $MgCl_2$ (PMB) and frozen at −80° C. In general, but particularly when using virulent Microbes (pathogenic), is recommended to kill the cells prior to further use, for example by treatment with formalin as described by Michalek and McGhee, 1977, and adjust concentrations to $10^8$ bacterial or fungal cells/ml or $10^7$ protozoa/ml. The preparation can be established to be sterile when no multiplication occurs upon inoculation on Sheep blood and Mitis Salivarius agars (DIFCO) or other adapted rich culture medium. Aliquots are stored at −80° C. Subsequently they are thawed rapidly at 37° C., and 1 g of whole cells is re-suspended with 1 g of micro-glass beads (0.17-0.18 mm) in 1 ml of PMB to which 3 μg/ml Dnase (SIGMA) is added. The cells are disrupted by shaking for three 2-minute cycles in a Braun homogenizer. Intact cells and debris are removed by two centrifugations (27.000×g followed by 47.000×g; 10 minutes each).

Preparation of ribosomes from fungi and protozoa follow essentially the same procedure but require adaptation of culture conditions and lysis methods. Given that culture conditions of cultivatable pathogenic Microbes are widely available in published literature, preparation of ribosomes from such Microbes is well within the possibilities of a person skilled in the art.

Integrity of the ribosomal subunits is important. In particular the stabilization of enclosed large ribosomal RNA's by divalent cations such as provided by $MgCl_2$, concentration which may need adaptation depending on the Microbe and extraction protocol, method which the man skilled in the art shall know to adapt. The ribosomes in the supernatant can be harvested by centrifugation at 180.000 to 250.000×g for 2 to 3 hr and then subjected to 5 successive washes in PMB at 180.000 to 250.000×g for 2 to 3 hr each. The ribosomal preparation is then clarified twice by two 20-min. centrifugations at 47.000×g and the supernatant is filtered through a sterile 0.45 μm Millipore filter (Millipore Filter Corp.). Non-dissociated (=intact) ribosomes can be prepared from gram-negative, Rnase-minus mutant bacteria such as *Escherichia coli* MRE600 following the method of Staehilin et. al., 1969, with modifications as described by M. M. Yusupov and A. S. Spirin. 1988. The preparations can then adjusted to, for example, 20 mg/ml on the basis of protein content by standard protein quantification methods, using, for example, bovine serum albumin as a standard, and maintained at −80° C. until used. Characterization of the ribosomal fraction and purity can be determined by spectral analysis at 235, 280 and 260 nm in order to determine the contamination of ribosomal RNA by DNA. polyacrylamide gel electrophoresis permits to evaluate the presence of ribosomal proteins and potential contaminating proteins. The degree of intactness can be evaluated by loading a sample of the original homogenate onto a 10% to 40% sucrose gradient, containing an appropriate concentration of Mg Cl$_2$ and centrifugation. The elusion profile of the sucrose gradient will show the different fractions: 100S=dimers of 70S ribosomes, 70S=intact ribosomes, 60S=interacting 50S and 30S ribosomal subunits, 50S=large ribosomal subunit, 30S=small ribosomal subunit, material less than 30S=degradation products and contaminants. In good preparations that target non-dissociated ribosomes, the 70S peak contains over 80% of all material. Optionally, the 70S peak containing the target non-dissociated ribosomes may constitute at least 50%, 60%, 70% or 90% of all material.

The term "isolated" requires that the material be removed from its original environment (e. g., the natural environment if it is naturally occurring). For example, a naturally-occurring polypeptide, antigen or Ribosomal Complex or ribosomal subunit present in a living animal is not isolated, but the same polynucleotide or DNA or polypeptide, separated from some or all of the coexisting materials in the natural system, is isolated. Such an antigen, polypeptide, Ribosomal Complex or ribosomal subunit could be part of a composition, and still be isolated in that the vector or composition is not part of its natural environment.

The term "purified" does not require absolute purity; rather, it is intended as a relative definition. Purification of starting material or natural material (e.g. antigen, polypeptides, ribosomal subunits or Ribosomal Complex) to at least one order of magnitude, preferably two or three orders, and more preferably four or five orders of magnitude is expressly contemplated. As an example, purification from 0.1% concentration to 10% concentration is two orders of magnitude. The term "purified" is further used herein to describe an antigen, polypeptide, ribosomal subunits or Ribosomal Complex which has been separated from other compounds including, but not limited to, polypeptides, antigens, or polynucleotides, carbohydrates, lipids, etc. The term "purified" may be used to specify the separation of monomeric polypeptides of the invention from oligomeric forms such as homo- or heterodimers, trimers, etc. A polynucleotide is substantially pure when at least about 50%, preferably 60 to 75% of a sample exhibits a single polynucleotide sequence and conformation. A substantially pure polypeptide, antigen, ribosomal subunit or Ribosomal Complex typically comprises about 50%, preferably 60 to 90% weight/weight of a polypeptide, antigen, ribosomal subunit or ribosomal RNA sample, respectively, more usually about 95%, and preferably is over about 99% pure. Polypeptide, antigen, ribosomal subunit or Ribosomal Complex purity, or homogeneity, is indicated by a number of means well known in the art, such as agarose or polyacrylamide gel electrophoresis of a sample, followed by visualizing a single band upon staining the gel. For certain purposes higher resolution can be provided by using HPLC or other means well known in the art.

Adhesins have been widely studied for many Microbes and protocols describing the preparation of Adhesins either directly from Microbes or after cloning of the Adhesin-coding genes in expression vectors, transformation of resulting expression cassettes into appropriate organisms or eukaryotic cells and heterologous production of said Adhesins, are available in the literature and can be adapted where needed by those skilled in the art. A few examples of microbial Adhesins useful in the preparation of Immunogenic Complex are: the products of *Staphylococcus aureus* genes fnbA and fnbB, encoding 110 and 98 kDa proteins respectively; the porin OmpC protein of *Salmonella typhimurium*; polypeptide segments PAK 128-144, PAO 128-144, KB7 128-144 and P1 126-148, corresponding respectively to amino acid sequences of the C-terminal receptor binding regions of four strains (PAK, PAO, KB7, P1) of *Pseudomonas aeruginosa* pilin protein are examples of polypeptide Adhesins; Colonization Factor Antigen CFA/II of entero-toxigenic *Escherichia coli*; full length *Streptococcus mutans* non-fimbrial cell surface antigen SA I/II; the polypeptide derived from SAI/Il, that spans the residues 1025-1044 in the C-terminal domain, is another example of a polypeptide Adhesin; WI-1 adhesin of *Blastomyces dermatitidis* yeast; surface Adhesin Fab1 of *Streptococcus parasanguis; Porphyromonas gingivalis* fimbrial proteins, fibrillous M-protein of Group A Streptococci; filamentous hemagglutinin of *Bordetella pertussis*.

It will be appreciated that viral antigens to be used in accordance with the present invention can be isolated and purified according to means known in the art. Examples of viral antigens that can be used in the Bacterio-viral Immunogenic Complex include the fusion (F) protein of respiratory syncytial virus (RSV); the attachment G glycoprotein of RSV; the antigen portion comprising the junction of the glycoprotein G with the fusion protein F of RSV; the central conserved domain of the G glycoprotein of (RSV) which spans the amino acids (N-terminal to C-terminal direction) 124 to 230; the hemagglutinin (HA) of influenza virus; the neuraminidase (NA) protein of influenza virus; the nucleoprotein (NP) of influenza virus; the AgD, SgD or CgD antigens of Bovine herpesvirus-1; glycoprotein B (gB) or glycoprotein D (gD); the VP4 antigen of Group A rotavirus; HA or nucleoprotein (NP) of measles virus; the S protein of Hepatitis B virus (HBV); the core protein, (HbcAg), or HbeAg or HbsAg of HBV; HCV proteins such as core, S, E1 and E2; glycoprotein gp 160 or envelope protein or the gag/pol, rev, tat or nef proteins of human immunodeficiency virus (HIV); the nucleoprotein of the lymphocytic choriomeningitis virus; the major capsid protein L1 of papillomavirus; glycoprotein of rabies virus; envelope protein or Vp4 or Vp6 or Vp7 of rotavirus; viral envelope (E) protein, the precursor for membrane (prM) protein and the non-structural protein NS1 of Murray Valley encephalitis virus (MVEV); the prM or E proteins of Japanese encephalitis virus.

To prepare Adhesin or viral antigen in large quantities and pure form, one can purify the Adhesin or viral antigen from the fermented Microbe or virus which naturally expresses said Adhesin or viral antigen. In cases where this is costly, inefficient or is undesirable for public health safety or other reasons, a preferred embodiment of the present invention is to clone and express the gene encoding the Adhesin or viral antigen in a heterologous organism such as *E. coli* (gram-negative bacterium), *Bacillus subtilis* (gram-positive bacterium) or *Saccharomyces cerevisiae* (baker's yeast). Classical recombinant DNA techniques for cloning, expressing a gene in adapted expression vectors and purifying the resulting protein are described in many laboratory manuals available to the person skilled in the art. Alternatively, and particularly when a polypeptide epitope of an adhesin protein or viral antigen is used, well-established peptide synthesis methods can be used to create ultra-pure polypeptides for use in the Immunogenic Complex. In examples below which focus on some other Adhesins, different methods to prepare Adhesins for use in Immunogenic Complex are described.

The optimal ratio of Adhesin or viral antigen/Ribosomal Complex in the Immunogenic Complex or Bacterio-viral Immunogenic Complex depends on several factors including the immunogenicity of the selected adhesin or antigen. Consequently, the optimal ratio of Adhesin or viral antigen to Ribosomal Complex in a vaccine is best determined empirically using appropriate animal models (e.g. mice, rats, rabbits, pigs, monkeys) by comparing immunogenicity and protection against target pathogen of Immunogenic Complex or Bacterio-viral Immunogenic Complex with different Adhesin-to-Ribosomal Complex ratios or viral antigen-to-Ribosomal Complex ratios. For example, the selected ratio's given in the examples which follow and other experiences allows to indicate that the ideal weight ratio of Ribosomal Complex to Adhesin for different Microbes, coupling reactions, delivery systems, pharmaceutical compositions and posologies, lies in the range of 0.05 to 20.

In cases where the Immunogenic Complex or Bacterio-viral Immunogenic Complex is not or is unlikely to be destabilized by solvents nor is to be exposed to excessive degradation such as in the Gastro-intestinal tract (GIT), then the ionic interactions between Ribosomal Complex and Adhesin or viral antigen fractions are generally sufficient for joint delivery to the MALT.

In some cases, in particular if no protective carrier or matrix is used and ionic interaction of RC and Adhesin or viral antigen are considered insufficient for joint delivery to the mucosal immune system, a preferred embodiment of the present invention is to covalently couple the Adhesins or viral antigen to the Ribosomal Complex. This can be achieved by various methods known to the experienced person in the art, such as by use of N-hydroxysuccinimidyl esters like disuccinimidyl suberate or N-Succinimidyl-(3-[2-pyridyl]-dithio) propionate (SPDP) or for example the use of 1-(3-dimethylaminopropyl)-3-ethylcarbodiimide (EDC) or bis imido esters such as dimethyladipimidate. The final choice may also be affected by whether or not the chosen linker is antigenic by itself: following linkers don't behave as hapten by themselves:

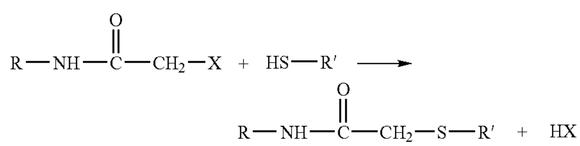

whereby: X = I or Br. Alternatively covalent linkage can be achieved by use of glutaraldehyde.

In a preferred embodiment of present invention for use as oral vaccine, the Immunogenic Complex or Bacterio-viral Immunogenic Complex is protected from the low pH environment and excessive degradation in the gastrointestinal tract (GIT) by enzymes such as pepsins, trypsin, chymotrypsin, elastase and carboxypeptidase, by means of incorporation in a carrier consisting of polymeric matrices such as for example chitosan and collagen or encapsulated in micro-particles such as for example liposomes and poly(lactic-co-glycolic acid) particles or in hydrogels such as for example poly(alginic acid), dextran cellulose, gelatin or albumin. The use of such protective carriers is well documented. The amount of carrier versus Immunogenic Complex or Bacterio-viral Immunogenic Complex employed in such vaccines will vary depending upon the exact carrier used. Adjustment and manipulation of established dosage ranges used with traditional carrier molecules for adaptation to the present invention is well within the ability of those skilled in the art, however it is preferred to keep the size of the micro-particles between 0.1 and 10 μm average diameter.

In one embodiment of the present invention, the Immunogenic Complex, Bacterio-viral Immunogenic Complex or Heterologous Immunogenic Complex are active principles in prophylactic vaccines against microbial species.

In another embodiment of the present invention, the Immunogenic Complexes, Heterologous Immunogenic Complex or Bacterio-viral Immunogenic Complex are derived from multiple Microbes or viruses have therapeutic use against microbial or viral infection, in disease management and in other cases where stimulation of the immune system is desirable. For example, the immuno-stimulatory effect of the Immunogenic Complex on Helper T-cell activation generally enhances the immune reaction of the host against the established pathogen. This may be of paramount importance for recovery of immuno-depressed subjects. In cases where the Micobes' pathogenesis strategy involves impairment of the host's immune defense by, for example, anti-phagocytosis activity or induced macrophage apoptosis or survival in the endocytic vacuole post macropinocytosis followed by cell-to-cell movement in an actin-dependent process, then the use of Adhesins expressed by such Microbes during their virulent phase, in particular those which use M-cells as entry port into host tissues, can be used in Immunogenic Complex of prophylactic as well as of therapeutic vaccines. Examples of Adhesins useful in treatment of such disease are: the Lpf gene product in specialized fimbriae of *Salmonella typhimurium* (these fimbriae are involved in specific adherence to M cells of murine Follicle Associated Epithelia); the ipa genes products of *Shigella flexneri*, the major secreted effectors of entry into epithelial cells and protein YadA of enteropathogenic Yersinia. Established gingivitis caused by penetration and colonization of multi-layered gingival pocket epithelial cells by *Porphyromonas gingivalis*, is an example where Immunogenic Complex, comprising *P. gingivalis* Ribosomal Complex and/or Adhesin, can be used in a therapeutic vaccine.

Microbes, from which Ribosomal Complexes and/or Adhesins can be prepared, include, but are not limited to, the following:

*Actinobacillus—Campilobacter consius actinomycetemcomitans—Capnocytophaga* sp.
*Bacille Calmette-Guérin—Chlamydia trachomatis*
*Bordetella pertussis—Eikenella corrodens*
*Enterococcus* sp.—*Neisseria gonorrhoea*
*Escherichia coli—Neisseria meningitidis*
*Eubacteruim* sp.—*Nocardia* sp.
*Haemophilus influenzae—Pasteurella multocida*
*Lactobacillus acidophilus—Porphyromonas gingivalis*
*Listeria monocytogenes—Prevotella intermedia*
*Mycobacterium vaccae—Pseudomonas aeruginosa*
*Rothia dentocarius—Streptococcus pyogenes*
*Salmonella typhi—Treponema denticola*
*Salmonella typhimurium—Vibrio cholera*
*Serratia marcescens—Wolinella recta*
*Shigella dysenteriae—Yersinia enterocolitica*
*Streptococcus mutans—Candida albicans*
*Streptococcus pneumoniae—Blastomyces dermatitidis*
*Plasmodium falciparum—Leishmania* sp.
*Trypanosoma cruzi—Entamoeba histolitica*

Pharmaceutical compositions can be prepared for prevention and treatment of infectious disease caused by Microbes or viruses. Such pharmaceutical compositions comprise Immunogenic Complex or Bacterio-viral Immunogenic Complex wherein the Immunogenic Complex or Bacterio-viral Immunogenic Complex is formulated with pharmaceutical carriers in pharmaceutically acceptably delivery forms such as liquids, aerosols, lyophilized powders, pills, creams and suppositories; some of which may contain compounds such as erythrosine, titanium dioxide, $Fe_2O_2$, D-mannitol, magnesium stearate, gelatin, oils, waxes, antibiotics or antiseptics for administration to animals and/or humans.

The dosage and route of administration depends to a large extend on the condition and weight of the subject being treated, as well as on the frequency of treatment. Regiments for boost immunizations, including dose may be influenced by the response of the initial prime inoculation and clinical judgement of the effect. While the above described Immunogenic Complex or Bacterio-viral Immunogenic Complex may be produced and formulated for injection (parenteral or intramuscular), it is particularly suited for delivery to buccal epithelia in a gel, to mucosal tissues of nose, mouth, eye and throat by spray of a liquid suspension, delivery to upper respiratory tract by dry or liquefied aerosol spray, delivery to the gastro-intestinal tract in protective matrix or microparticle, formulated in a pill, and delivery to rectal, vaginal and uteral mucosa incorporated in a gelatinous capsule or suppository.

While the invention has been described and illustrated herein by references to the specific embodiments, various specific material, procedures and examples, it is understood that the invention is not restricted to the particular material combinations of material, and procedures selected for that purpose. Indeed, various modifications are intended to fall within the scope of the appended claims.

It is further to be understood that all base sizes or amino acid sizes, and all molecular weight or molecular mass values, given for nucleic acids or polypeptides are approximate, and are provided for description.

The following examples are offered by way of illustration and are not intended to limit the invention in any matter.

EXAMPLE 1

Preparation, Administration and Evaluation of a Vaccine against Entero-toxigenic *Escherichia coli* (ETEC) in Pigs, Based on Immunogenic Complex Entero-toxigenic *Escherichia coli* (ETEC) causes diarrhea in domesticated animals such as pigs and in humans. In humans there are an estimated 650 000 000 cases annually in developing countries resulting in 500 000 deaths predominantly babies, small children and elderly. An effective, well-tolerated vaccine is currently not available and would benefit those mentioned above, including the millions of travelers to these high-risk areas. This example illustrates the use of Immunogenic Complex as a vaccine against ETEC in pigs.

1. Bacterial culture: The hemolytic *E. coli* strains isolated from pigs infected and with symptoms caused by Entero-toxigenic *E. coli* can be used, such as strain GIS 26, serotype 0149:K91:F4ac, $LT^+STa^+STb^+$ (Laboratory of Veterinary Immunology, Fac. of Veterinary Medicine, Univ. of Gent, Belgium). The bacterial strain is cultured on brain heart infusion agar (Oxoid Laboratories) during 18 hours at 37° C., after which the expression of Fimbriae (in this case, F4ac fimbriae) is best tested in an agglutination assay using fimbriae-specific antibodies (in this case, F4ac-specific Mab [clone CVI F4ac-5, ID-DLO, Lelystad, the Netherlands]). An individual $F4ac^+$ colony is transferred to tryptone soy broth (DIFCO Laboratories) and incubated at 37° C. for 18 hours while gently shaking at 85 rpm. Subsequently, the bacteria are collected by centrifugation (3,000×g, 30 min., 4° C.), washed in phosphate-buffered saline (PBS; 10 mM sodium phospate, pH 7.4, 150 mM sodium chloride) and suspended in the same buffer. The concentration of bacteria is determined by measuring the optical density of the bacterial suspension at 660 nm (OD 660). An OD 660 of 1 equals $10^9$ bact./ml, as determined by counting colony-forming units. Subsequently, the concentration is adjusted to $10^{11}$ bacteria/ml.

2. Isolation of Adhesins from native F4 fimbriae of Entero-toxigenic *Escherichia coli* (ETEC): Isolation of fimbriae can be done essentially as described by Jacobs and de Graaf, 1985, with slight modifications. Briefly, the bacterial suspension is homogenized, followed by centrifugation to remove larger fragments. The fimbriae, solubilized in the supernatant, are precipitated with 40% (wt/vol) ammonium sulfate. After centrifugation, the precipitate pellet is dissolved, dialyzed overnight against ultra pure $H_2O$. Purification of Fae G from the fimbrial protein complex can be done by anion exchange chromatography (AEC) using a Bio-scale Q2 column (BIO-RAD Laboratories). Hereto, the fimbrial solution is loaded onto the column using PBS (pH 7.4, 10 mM sodium phospate, pH 7.4, 150 mM sodium chloride) as buffer. At pH 7.4, the F4ac fimbriae have a net negative charge and will be retained on the column. Elution by increasing the NaCl concentration in the PBS allows collection in 0.5 ml fractions which are dialyzed overnight against a phosphate buffer (0.1M, pH 7.0) containing 0.01 M $MgCl_2$ (PMB) using ultra pure $H_2O$ as solvent. The protein concentration can subsequently be measured and concentration of aliquots can be set at 30 mg/ml.

3. Preparation of Immunogenic Complex from Entero-toxigenic *Escherichia coli* (ETEC): Ribosomal Complex is prepared from log phase culture of *E. coli* strain GIS 26, as described earlier and mixed with Adhesin fraction in a ratio 10/1 [wt/wt].

4. Procedure to prepare carboxymethylethylcellulose (CMEC) coated poly[dl-lactide-co-glycolide] (PLG) micro-particles containing the Immunogenic Complex (IC) prepared from Entero-toxigenic *Escherichia coli* (ETEC): Briefly, an aqueous solution of IC (40 ml, 20 mg/ml) is emulsified with 200 ml of a 4% solution of PLG copolymer (Resomer RG 503, Mw 34,000) in dichloromethane (DCM) using a Silverson homogenizer for 3 min. at 10,000 rpm to produce the primary emulsion. The resulting w/o emulsion is then re-emulsified for 10 min. at high speed with a solution of CMEC to produce a double emulsion (w/o/w). Different concentrations of CMEC are best tested (2.5%-8%), adding 0.2 M NaOH to yield a final pH of approximately 6. The w/o/w emulsion is stirred magnetically for 12 h at room temperature and under reduced atmospheric pressure to allow solvent evaporation. The micro-spheres are isolated by centrifugation, washed 3 times in double distilled water and lyophilized. The product can be stored in a desiccator at a temperature of −18 Celsius. Particles can be sized by laser difractometry using a Malvern 2600D laser sizer. Particle size is expressed as volume mean diameter. Encapsulation (10%-50% efficiency) can be achieved in enteric-coated PLG micro-particles with volume average diameter of less than 10 μm.

5. Procedure to orally vaccinate pigs with Immunogenic Complex derived from Entero-toxigenic *Escherichia coli* (ETEC) in carboxymethylethylcellulose (CMEC) coated poly[dl-lactide-co-glycolide] (PLG) micro-particles.

a) Pigs: 35 F4-seronegative pigs (Belgian Landrace×Piétrain), 9 weeks of age, can be used. They are weaned at the age of 4 weeks, subsequently housed in isolation units and fed ad libitum, with sterilized feed ratios. At the end of the experiment, all animals are killed by intravenous injection of pentobarbital (24 mg/kg); Nembutal, Sanofi Santé Animal) followed by exsanguination.

b) Oral administration of IC in CMEC coated PLG microparticles: A first group of 15 pigs is orally given IC in CMEC coated PLG micro-particles (10 mg/pig/day), whereas a second group of 15 pigs receives CMEC-coated PLG micro-particles without IC content. The antigens and the placebo are respectively given orally for 3 successive days and once again on day 15 to the 2 sets of 15 pigs. They are administered orally in 10 ml $H_2O$ after depriving the animals of food and water for 3 hours. Subsequently the pigs are deprived for an additional 2 hours. 5 untreated pigs are slaughtered on day 0; 5 pigs of respectively the experimental and the placebo group are slaughtered at day 22 and another set of 5 pigs of respectively the experimental and the placebo group are slaughtered on day 30 post initiation of the experiment.

c) Oral administration of ETEC: The 5 remaining pigs of respectively the experimental and the placebo group are orally infected with a virulent $F4^+$ ETEC strain as described by Cox et al., 1991 on day 18. Prior to the oral infection, the animals are treated with chloramphenicol (200 mg/kg) solubilized in milk during 6 hours and starved overnight. Gastric pH is neutralized with $NaHCO_3$ (3% [wt/vol.]) in distilled water prior to administration of $10^{10} F4^+$ ETEC.

6. Procedure to evaluate vaccination efficacy of the Immunogenic Complex (IC) derived from Entero-toxigenic *Escherichia coli* (ETEC) in carboxymethylethylcellulose (CMEC) coated poly[dl-lactid-co-glycolide] (PLG) micro-particles in post-weaning pigs for the control of entero-toxigenic *E. coli* (ETEC):

a) Sample preparation for serum IgA and IgG response measurement: Directly after slaughter, IC-specific antibodies and antibody-secreting cells (ASC) can be determined in the blood and the number of ACS's can also be measured in the spleen, bronchia, mesenteric and retro-pharyngeal lymph nodes and Peyer's patches. The jugular vein of the pigs is drained for blood samples. After 18 hours incubation at room temperature, serum is collected, inactivated at 56° C. for 30 minutes and then treated with Kaolin (SIGMA) to decrease the background reading in ELISA: 4 vol. of kaolin suspension (25% [wt/vol.] in phosphate-buffered saline (PBS) are added to 1 vol. of serum and incubated at room temperature for 30 min. The suspension is centrifuged at 5500×g for 10 min. and the supernatant is diluted in ELISA dilution buffer (PBS+0.2% [vol./vol.] Tween 20, yielding a final serum dilution of 1/10.

b) Sample preparation for Antibody Producing Cells (APC): Peripheral blood monomorphonuclear cells (MC) are isolated by density gradient centrifugation (500×g at 18° C. for 45 min.) on NYCOMED Pharma AS Lymphoprep. After lysis of erythrocytes in ammonium chloride (74.7% [wt/vol.] and subsequent centrifugation (380×g at 4° C. for 10 min.), the pelleted cells are washed and resuspended at $10^7$ cells/ml in leukocyte medium [RPMI-1640] of GIBCO BRL containing fetal calf serum (FCS, 10% [vol./vol.]); β-mercaptoethanol ($1/5\times10^5$ M), non-essential amino-acids, Na-pyruvate (100 μg/ml), L-glutamine (292 μl/ml), penicillin (100 IU/ml), streptomycin (100 μg/ml) and kanamycin (100 μg/ml)]. MC's from the aseptically dissected spleen and lymph nodes are isolated by teasing the tissue apart, followed by lysis of erythrocytes with ammonium chloride. After centrifugation (380×g at 4° C. for 10 min.), the pelleted cells are washed and resuspended in leukocyte medium at 107 cells/ml. Isolation of MC from Peyer's patches is achieved by aseptically dissecting pieces of the small intestine, washing them 3× in PBS without calcium or magnesium (CMF buffer) and once with CMF buffer with EDTA (3.7% [wt/vol.]. Subsequently, Peyer's patches MC are collected by scraping the Peyer's patches, washed and resuspended in leukocyte medium as described above for peripheral blood MC.

c). ELISA for IC-specific IgG and IgA: The wells of a 96 well micro-titer plate (NUNC, Polysorb Immuno Plates) can be coated with a IC-specific monoclonal antibody (Mab), here called CVI-IC, at a concentration of 1 μg/ml coating buffer (carbonate-bicarbonate buffer, 50 mM, pH 9.4 or PBS). After 2 hours of incubation at 37° C., the remaining binding sites are blocked for 30 min. with PBS supplemented with 0.2% (vol./vol.) Tween 20 at room temperature. The IC is subsequently added to the wells at a concentration of 50 μg/ml of ELISA dilution buffer and incubated for 1 hour at 37° C. Treated sera (for IgG's) are added, series of twofold dilutions, starting from 1/10, are made in ELISA dilution buffer, and plates are incubated for 1 hour at 37° C. Thereafter, plates are treated for 1 hour at 37° C. with optimal dilutions of anti-swine IgG- and IgA-peroxidase conjugates. Conjugates are prepared by coupling IgG- and IgA-specific Mab's to peroxidase using the peroxidase labeling kit by Boehringer-Mannheim. The substrate, TMB, is added and the optical density is spectrophotometrically measured at 405 nm (OD405) after 15, 30 and 60 minutes incubation at 37° C. Between each incubation step, plates are washed 3× with PBS-T. For secreted IgA's, fresh feces are collected, treated with protease inhibitors and IgA's extracted. A good protocol is described by Externest et al., 2000. Infect. Immun., 68: 3830).The obtained OD405 of all preparations (dilution 1/10) at day 0 are averaged and the Standard Deviation can be considered as the cutoff value. The antibody titer is the inverse of the highest dilution, which still has an OD405 higher than the calculated cutoff value.

d) Elispot assay for IC-specific IgG- and IgA secreting cells: IC-coated plates are prepared as above described. Subsequently, MC suspensions at a concentration of $10^7$ cells/ml leukocyte medium are added to 10 wells (100 μm/well), and plates are incubated for 3 hours at 37° C. in a humidified 5% CO2 atmosphere. After removing cells by three subsequent washes with PBS-T, plates are treated with anti-swine IgG and IgA conjugates (see PLISA procedure) for 1 hour at 37° C. Unbound conjugates are removed by three BPS-T washes and the substrate solution, consisting of 4 volumes of 3-amino-9-ethylcarbazole (AEC) working solution [0.67 ml AEC stock solution (0.4% [wt/vol.] in dimethylformamide) in 10 ml Na acetate (0.1 M, pH 0.2)+10 μl 30% H2O2] and 1 volume of 3% (wt/vol.) low-melting-point agarose (Biozym), is added. Reactive spots are counted with an inverted microscope after plates have been incubated in the dark for at least overnight at room temperature. For each MC suspension, spots in 10 wells ($10^6$ MC/well) are counted, so that finally the amount of ASC per $10^7$ MC is obtained.

7. Immune response following oral immunization with IC in CMEC coated PLG micro-particles:

a) Humoral immune response: The humoral immune response after the oral administration can be evaluated by determining the antigen-specific serum antibody titer on days 0, 7, 15, 22 and 30 post initiation of the experiment. A substantial increase of the antigen-specific IgA and IgG response versus controls can already be noted on day 7, which continues to increase strongly on day 15 and day 22, after which further rate of increase may reduce.

Results show that (1) the Immunogenic Complex (IC) derived from Entero-toxigenic *E. coli* (ETEC) in carboxymethylethylcellulose (CMEC) coated poly[dl-lactide-co-glycolide] (PLG) micro-particles induces a strong humoral IgG and IgA response in immunized pigs and (2) antibody titers induced by PLG micro-particles (control) remain flat over the entire period of the experiment and do not in themselves induce specific immunity.

b) Production and localization of Antigen-specific Antibody-secreting Cells: In order to localize and quantify antigen-specific antibody-secreting cells (ASC), the number of IC-specific ASC (IgG and IgA) can be determined at days 0, 22 and 30 post initiation of the experiment in blood, spleen, bronchia, mesenteric and retro-pharyngeal lymph nodes and Peyer's patches. Induction of both IgG and IgA ASC's are already apparent after 15 days in Peyer's Patches.

Results demonstrate that (1) CMEC-coated PLG micro-particles in themselves do not induce IC-specific ASC's, (2) Immunogenic Complex-specific IgA ASC's are significantly present after 22 days in MLN, spleen and blood serum and retain their levels after 30 days, (3) Immunogenic Complex-specific IgG ASC's are also significant after 22 days in MLN, RPLN, (4) induction in Peyer's Patches of the intestine (target organ of ETEC) is approximately 2 to 10 fold higher than in other tissues that showed significant induction, (5) induction of IC-specific ASC's in mucosal tissues which have not been in contact with the antigen (e.g. bronchia) remains low (6) inductive immune tissues (e.g. spleen) as well as humoral (blood) and mucosal (Peyer's Patches) effector parts of the immune system show evidence of strong immune response upon IC administration.

c) Immunity of vaccinated pigs following oral administration with IC in CMEC-coated PLG micro-particles: The pigs infected with F4+ ETEC on day 18 can be analyzed for (1) clinical symptoms (diarrhea), (2) relative weight gain versus the pig group vaccinated with the same antigens but not ETEC-inoculated, and (3) presence of ETEC in feces.

Results show that (1) IC vaccinated pigs do not develop diarrhea, (2) IC vaccinated pigs do not show less weight gain over time in comparison with the non-inoculated group, (3) IC vaccinated pigs have ETEC counts in their feces which are significantly lower than those of pigs mock-vaccinated with CMEC-coated PLG micro-particles, (4) mock-vaccinated pigs develop diarrhea within days of ETEC inoculation, show reduced weight gain versus the non-inoculated pigs, (5) recovery of mock-vaccinated pigs can occur within 10 days but weight gain remains lagging throughout the measured period (45 days).

Jointly, the above illustrates that immunization of pigs against entero-toxigenic *E. coli* (ETEC) with Immunogenic Complex prepared from ETEC is effective in inducing a strong, specific and protective humoral and mucosal immune response against ETEC.

EXAMPLE 2

Preparation, Administration and Evaluation of a Vaccine Against *Candida albicans* Based on Immunogenic Complex In this example, an Immunogenic Complex (IC) is prepared that consists of Ribosomal Complex of *Candida albicans* and of two different Adhesins of *C. albicans*, ALA1 and HWP1, which can be prepared from 2 strains of a heterologous organism, *Saccharomyces cerevisiae*, each of which incorporates an expression vector that carries the corresponding *C. albicans* genes (Ala1 and Hwp1) encoding for the respective Adhesins.

1. Culture of *Candida albicans* IPca1809: A virulent *Candida albicans* strain, preferentially isolated from an infected patient is best used as source of components of the Immunogenic Complex. Here, strain IPca1809 (originating from an HIV positive male individual with severe buccal and pharyngeal candidiasis, Quint, France) is used. It can be maintained on yeast extract agar. For preparation of Ribosomal Complex, the strain is transferred to liquid culture medium in 6 liter badges, consisting of 1.17% [wt/vol] yeast carbon base, 1% bovine serum albumin (YCB-BSA medium) and cultured in a gyratory shaker (New Brunswick Scientific Co.) at 150 rpm at 27° C. until mid-log phase.

2. Preparation of Ribosomal Complex: *C. albicans* cells (in 20 mg wet weight aliquots) are suspended in an equal weight of Tris-magnesium-ammonia buffer [0.05 M $NH_4Cl$, 0.01 M magnesium acetate, 0.01 Tris-HCL (pH 7.4)] and passed through a French press twice at 16.000 lb/inch$^2$. Bentonite is added to a final concentration of 2 mg/ml, and the suspension is centrifuged at 18.000 rpm (30.000 g) for 30 min. at 2° C. in a Sorvall SS34 rotor. The ribosomes are sedimented from the obtained supernatant by a second centrifugation at 40.000 rpm (105.000 g) for 90 min. at 4° C. in a Beckman 50 Ti rotor. The pellet is resuspended in Tris-magnesium-0.05 M $NH_4$ buffer and the ribosomes are sedimented as before. The pellet is resuspended in Tris-magnesium-0.25 M $NH_4$ buffer [0.25 M $NH_4Cl$, 0.01 M magnesium acetate, 0.01 Tris-HCL (pH 7.4)] to give a concentration of 80 $OD_{260}$ units/ml. The ribosomal suspension is clarified by centrifugation at 5000 rpm (2000 g) for 10 min. in a Sorvall SS34 rotor. The clarified ribosomal suspension (approximately 25 ml) is absorbed at 4° C. to a 2.5×50 cm column of DE23 (Whatman) which has been equilibrated with Tris-magnesium-0.25 M $NH_4$ buffer. The column is washed with 1 liter of Tris-magnesium-0.25 M $NH_4$ buffer at a flow rate of 300 ml per hour. The ribosomes are then eluted with Tris-magnesium-0.60 M $NH_4$ buffer [0.60 M $NH_4Cl$, 0.01 M magnesium acetate, 0.01 Tris-HCL (pH 7.4)] at a flow rate of 200 ml/h. The portion of the column elute containing ribosomes is recognized by its bluish opalescence. More than 80% of the $OD_{260}$ units can be recovered in less than 50 ml of elute. Ribosomal Complex, containing ribosomes dissociated into their 18S and 28S subunits, can be obtained in suspension by dialysis in 0.01 mM $MgCl_2$, 0.1 M NaCl, and 0.01 Tris-HCl (pH 7.4).

3. Preparation of *Candida albicans* Adhesins ALA1 and HWP1 upon over-expression in *Saccharomyces cerevisiae*: Industrial scale production of *Saccharomyces cerevisiae* is well established. Here we describe the inducible expression and extraction of heterologous ALA1 and HWP1 from Baker's Yeast.

a) DNA manipulations: DNA modifying enzymes and restriction enzymes can be purchased from New England Biolabs Inc. (Beverly, Mass.) and are used according the vendor's instructions. DNA fragments are purified after being resolved in a 1% low-melting-point agarose gel by using the Qiagen gel extraction kit according to the vendor's instructions (Qiagen, Inc. Chatsworth, Calif.). Plasmid DNA from yeast is isolated by the method described by Hoffman and Winston, 1987.

b) Strains and transformation: A virulent *C. albicans* strain such as IPca1809 can be used. The strain is maintained on Sabouraud (SAB) dextrose agar plates (Oxoid Ltd., Basingstoke, UK). For DNA isolation, cultures are grown in 100 ml SAB broth for 2 days at 27° C., washed in sterile water, and resuspended in 4 ml of lysis buffer (0.2 M NaCl, 0.4% sodium dodecyl sulfate, 0.1 M Tris- Cl [pH 7.5], 5 mM EDTA [pH 8]). Equal volumes of phenol (pH8) and glass beads are added, and the mixture is vortexed for 10 min. DNA is extracted twice with phenol-chloroform-isoamyl alcohol (25:24:1, vol./vol./vol.) at pH 8 and twice with chloroform-isoamyl alcohol (24:1, vol./vol.) and precipitated with 2.5. volumes of ethanol. DNA concentrations can be determined on a GeneQuant II spectrophotometer. *Saccharomyces cerevisiae* strain YPH499 (MATa ura3-52 lys2-801$^{amber}$ade2-101$^{ochre}$trp1-Δ63his3-Δ200leu2-Δ1), derived from the American Type Culture Collection (ATCC) can be used but other laboratory strains, preferentially equally devoid of adhesive properties but better adapted for industrial fermentation, can also be used. For long-term storage, all stocks can be maintained frozen in 20% glycerol. Media for growing Saccharomyces cerevisiae strains have following composition: YPD (1% yeast extract, 2% peptone, 2% glucose), YPGAL (1% yeast extract, 2% peptone, 2% galactose), and synthetic defined medium consisting of 0.67% yeast nitrogen base and 2% glucose with appropriate amino acid supplements (50 μg/ml). *S. cerevisiae* YPH499 is transformed with plasmid DNA by the lithium acetate method (Gietz R. D. and R. H. Schiestl, 1995). Competent *E. coli* cells (XL10-Gold) can be purchased from Stratagene (La Jolla, Calif.) and transformed with a plasmid according to the vendor's instructions. *E. coli* is grown at 37° C. in Luria-Bertani broth (1% NaCl, 1% tryptone, 0.5% yeast extract).

c) Construction of plasmids and 2 *S. cerevisiae* strains expressing respectively ALA1 and HWP1 upon galactose induction:

1. Construction of a vector plasmid replicating both in *E. coli* and *S. cerevisiae*: The plasmid p414GAL1, containing the galactose-inducible promoter, originating from ATCC can be used as source for the expression cassette: it is restricted with SacI & SnaBI and sticky ends are made blunt using T4 DNA polymerase. The blunt-ended SacI-SnaBI fragment, containing the TRP1 marker, the GAL1 promoter and multiple cloning sites, is gel purified. A plasmid such as pAUR112 (Gaur N. K. et al., 1999) can be used as source for construction of a dual host vector: In case of pAUR112, the XhoI-BgIII fragment is blunt-ended with T4 DNA polymerase, dephosphorylated and also gel purified. This DNA fragment contains the β-lactamase gene for selection in *E. coli* and sequences for replication in both *E. coli* and *S. cerevisiae*. The plasmid pKG112 is obtained by ligation of these two fragments and can be transformed into *E. coli*.
2. Cloning of the coding sequence of the Ala1 gene into pKG112: This can be done by PCR amplification from total DNA extracted from *C. albicans* virulent strain IPca1809, using appropriate primer sets based on Ala1 DNA coding sequences (GenBank database, accession number AF025429). Standard PCR procedures, well documented and known to the man in the Art can be used. The obtained blunt-end fragment is ligated to the SmaI linearised and dephosporylated pKG112 vector. The plasmid that contains the Ala1 gene in the right orientation versus the GAL1 promoter is called pIP114 (determined after transformation into *E. coli*). Both DNA strands can be sequenced for verification.
3. Cloning of the coding sequence of the Hwp1 gene into pKG112: This can also be done by PCR amplification from total DNA extracted from a *C. albicans* strain like IPca1809, using appropriate primer sets based on Hwp1 DNA coding sequences (GenBank database, accession number U64206). The blunt-end fragment is ligated to the SmaI linearised and dephosporylated pKG112 vector. pIP113 is called the plasmid that contains the Hwp1 gene in the right orientation versus the GAL1 promoter, as can be determined after transformation into *E. coli*. Both DNA strands of the Hwp1 gene can be sequenced in similar fashion as the Ala1 gene.
4. Transformation into *S. cerevisiae*: Plasmid DNA prepared from *E. coli* is transformed into a yeast strain such as *S. cerevisiae* YPH499, and the cell pellet is suspended in 5 ml of YPGal and grown at 28° C. for 20 h. Cells are collected and washed three times with 5 ml of TE buffer (10 mM Tris-HCL, pH 7.0; 1 mM EDTA) and then suspended in 1 ml of TE buffer. *S. cerevisiae* cells, transformed with respectively pIP114 and pIP113, express upon subculture in YPGa1 (1% yeast extract, 2% peptone, 2% galactose) respectively the ALA1 and HWP1 proteins. The yeast strains will further be called respectively YPH499-114 and YPH499-113.

d) Extraction and purification of ALA1 and HWP1 from respectively *S. cerevisiae* strain YPH499-114 and YPH499-113: For preparation of the recombinant proteins ALA1 and HWP1 from *S. cerevisiae* YPH499-114 and YPH499-113, these yeast strains, priorly maintained on YPD, containing 100 μg/ml aureobasidin A, can be transferred to YPGa1 liquid medium in 1 liter flasks and be cultured in a gyratory shaker (New Brunswick Scientific Co.) at 150 rpm at 30° C. until mid-log phase. Cell wall proteins can be released by digestion with β1-3 glucanase (lyticase, Sigma Chemical, MO, USA) in a rapid crude digest (RCD) procedure as follows: Cells are suspended at $1\times10^9$ cells ml$^{-1}$ in 55 mM NaPO$_4$ pH 7.2 buffer containing 250-500 U enzyme ml$^{-1}$ and protease inhibitors (1 mM EDTA, 0.2 phenylmethyl-sulphonyl fluoride (PMSF), 1 μm leupeptin and 1 μm pepstatin). Protein release can be monitored every 5 min. with the Coomassie Plus Protein Assay (Pierce Chemical, Rockford, Ill.) on supernatant fluid from 50 μl portions of the digest. Optimal digest conditions, which minimize cytoplasmic contamination, are best determined empirically. When 0.5 mg of protein per ml is reached, all cells are removed from the digest by centrifugation (2×10 min., 14000 g). The supernates can be stored frozen at −20° C. until purification. Upon thawing for purification of the proteins, protein inhibitors are replenished. Substantial quantities of cell surface protein are lost by dialysis in for example a Micro Pro-Di-Con apparatus (Spectrum Medical Industries, Tx, USA), against deionized water (pH 7) containing PMSF, using regenerated cellulose or cellulose ester membranes (6000 molecular weight cut-off). It is therefore recommended to only use this method for production of analytical quantities of ALA1 and HWP1. This is useful for the establishment of reference samples after identity confirmation by, for example, Matrix Associated Laser Desorbtion/Ionization Time-of-Flight (MALDI-TOF) Mass Spectrometry, a method for protein identification now well understood for persons experienced in the Art. Reference samples can serve for production of antibodies and as calibration reference in more quantitative purification methods such as ion-exchange chromatography followed by hydrophobic interaction chromatography in a low-pressure system, essentially as described here below:

1. Ion-exchange Chromatography: The thawed supernates, replenished with protein inhibitors can be pooled to up to 3 liters per column run. Solid NaCl is added to 0.1M. The supernate is vacuum filtered, degassed through a 0.2

μm filter, and loaded at a rate of 17.5 ml/min. onto an XK 16/20 column containing 20 ml of Source 30Q anion exchange media (Pharmacia Biotech, NJ, USA) pre-equilibrated with Buffer A (20 mM Tris, 0.1 M NaCl, pH 7.5) The column is washed with 5-7 vol of Buffer A, and the proteins are eluted at 12 ml/min with a linear gradient (0-100%) of Buffer B (20 mM Tris, 0.7 M NaCl, pH 7.5). Eluates from the column can be monitored by inline UV detection using a Gradifrac system (Pharmacia). The peaks corresponding to ALA1 or HWP1, depending on whether strain YPH499-114 or YPH499-113 is subject to extraction of recombinant protein, are collected in 3 ml fractions and are analyzed for content and purity by SDS-poly-acrylamide gel electrophoresis (PAGE). Fractions can be frozen at −20° C. until ready to be concentrated.

2. Hydrophobic interaction chromatography (HIC): Appropriate ion-exchange fractions are pooled, and protease inhibitors are again introduced as above. Solid $(NH_4)_2SO_4$ is added to bring the sample to 0.2 M that is subsequently vacuum- or syringe-filtered through a 0.2 μm filter. The filtered sample is loaded at 2 ml/min into a XK26/20 column containing 30 ml of phenyl-Sepharose high-performance HIC medium (Pharmacia) pre-equilibrated with Buffer C (20 mM Tris, 1.0 M $[NH_4]_2SO_4$, pH 7.5). Washing and elution is initiated using a two-step gradient as follows. For step 1, a linear gradient of 0-50% can be established with Buffer D (20 mM Tris, pH 7.5) across 40 ml and then held at 50% Buffer D across 20 ml for an additional wash. For step 2, a linear gradient of 50-100% Buffer D is established across 80 ml and then held at 100% buffer D across 50 ml, or until all of either ALA1 or HWP1 is eluted from the column. As above, peak fractions are collected in 3 ml volumes and analyzed by SDS-PAGE. HIC fractions can be kept frozen at −20° C. until ready for concentration.

e) Concentration and analysis: Desired HIC fractions with either ALA1 or HWP1 proteins are (each separately) pooled and concentrated by centrifugation at 4° C. in, for example, a CENTRIPREP-10 (Amicon, Mass., USA). Purified protein can be quantified by measuring the OD280 of samples and using a correlation factor based on the amino acid/DNA sequence or the BCA assay (Pierce, Ill., USA).

4. Preparation of Immunogenic Complex with *Candida albicans* Ribosomal Complex and Adhesins ALA1 and HWP 1: Ribosomal Complex, prepared from *C. albicans* as described earlier can be mixed with ALA1 and HWP1 proteins in a ratio 18/1/1 [wt/wt]. The Immunogenic Complex is subsequently dialyzed in 0.01 mM $MgCl_2$, 0.1 M NaCl, and 0.01 Tris-HCl (pH 7.4) and stored lyophilized until use.

5. Procedure to prepare formulated IC from *Candida albicans* in Chitosan-EDTA Bowman-Birk Inhibitor conjugate (CEBBI) tablets: 18.15 g of EDTA (ethylene-diamine-tetra-acetic acid; Sigma, St. Louis, Mo.) are dissolved in 100 ml of demineralised water and the pH-value adjusted to 6.0 with 5 N NaOH. To this solution 100 ml of an aqueous solution of 1% (w/v) chitosan HCL pH 6.0 (poly-[1-4]-β-D-glucosamine; Sigma, St-Louis, Mo.) and 5 ml of an aqueous solution of 2.27 g of EDAC (1-ethyl-3-(dimethylaminopropyl) carbo-diimide hydrochloride; Sigma, St-Louis, Mo.) are added. The reaction mixture is incubated at room temperature under permanent stirring for 12 h. The resulting conjugate is isolated by exhaustively dialyzing against demineralised water, 50 mM NaOH and once more against demineralised water. The purified product is precipitated by pouring the dialyzed polymer solution rapidly into an unstirred bath of non-solvent (acetone) at solvent to non-solvent ratio of 1:200, washed in acetone, and air-dried. The dried polymer can be stored at room temperature until use. 120 mg of this polymer are dissolved in 20 ml of demineralised water. EDAC and SNHS (sulfo-N-hydroxy-succinimide; Pierce, Oud-Beijerland, Nl) are added in a final concentration of 0.1 M and 5 mM, respectively, and the reaction mixture is incubated for 60 min. at room temperature under permanent stirring. Thereafter, 12 mg of previously demineralised (PD10 column; Pharmacia, Uppsala, Sweden) Bowman-Birk Inhibitor (BBI) is added, and the reaction allowed to proceed for 12 h. The reaction mixture is dialyzed for 6 h against demineralised water and then centrifuged for 30 min at 17.000 g (Sorvall RC5C, Dupont). The supernatant, containing the unbound inhibitor and coupling reagent, is discarded. The remaining pellet of the polymer-BBI conjugate is diluted with an at least 10-fold amount of demineralised water, centrifuged and the supernatant removed again. This purification step is repeated 10 times. The isolated polymer-BBI conjugate is precipitated in acetone as described above and stored at −20° C. until use. Lyophilized IC is added at 1% (w/w) to chitosan-EDTA (55%), chitosan-EDTA BBI conjugate (14%) and D-mannitol (30%), homogenized in a mortar and pressed (Hanseaten, Hamburg, Germany) to 250 mg pellets. As controls one can use tablets prepared identically but with following difference: no IC added and Chitosan-EDTA concentration at 56%.

6. Procedure to orally vaccinate pigs with Immunogenic Complex derived from *Candida albicans* in Chitosan-EDTA Bowman-Birk Inhibitor conjugate (CEBBI) tablets:

a) Pigs: 35 pigs (Belgian Landrace.times.Pitrain), 9 weeks of age can be used. They are weaned at the age of 4 weeks, subsequently housed in isolation units and fed ad libitum with sterilized feed ratios. At the end of the experiment, all animals can be killed by intravenous injection of pentobarbital (24 mg/kg); Nembutal, Sanofi Sant Animal) and be exsanguinated. Prior to vaccinations, the presence or absence of pre-existing candidiasis needs to be evaluated. This can be done by evaluation of presence/absence in unstimulated saliva aliquots: Yeast isolates can be identified as *C. albicans* using the API 32C AUX system (bioMerieux, Lyon, France), CHROMAGAR *Candida* (CHROMAGAR, Paris, France). All pigs used for the experiment should be *Candida* negative.

b) Oral administration of IC in CEBBI tablets: A first group of 15 pigs is orally given IC in CEBBI tablets (1 tablet/pig/day), whereas a second group of 15 pigs receives CEBBI tablets without IC content. The antigens and the placebo are respectively given orally for 3 successive days and once again on day 15 to the 2 sets of 15 pigs. The antigens are administered orally with forceps immediately followed by forced drinking of 100 ml $H_2O$ after depriving the animals of food and water for 3 hours. Subsequently the pigs are deprived for an additional 2 hours. 5 untreated pigs are slaughtered on day 0; 5 pigs of respectively the experimental and the placebo group are slaughtered at day 22 and another set of 5 pigs of respectively the experimental and the placebo group are slaughtered on day 30 post initiation of the experiment.

c) Oral administration of *Candida albicans*: The 5 remaining pigs of respectively the experimental and the placebo group are orally infected with the virulent *C. albicans* strain on day 18 (in this case IPca1809). Prior to the oral infection, the animals are starved overnight and subsequently allowed to chew on a moisturized thick cotton cloth (25 cm×50 cm) firmly fixed at one end to avoid swallowing and which is prior to drying, drenched in a solution of 20% glucose in milk and $10^9$ ml *C. albicans* cells. All pigs are presented such cloths until they have chewed and sucked on them for approximately 5 to 10 minutes.

7. Procedure to evaluate vaccination efficacy of the Immunogenic Complex (IC) in pigs for the control of *C. albicans*.
  a) Sample preparation for Ig response measurement: Directly after slaughter, IC-specific antibodies can be determined in saliva and in the blood and the number of antibody-secreting cells (ACS) can be measured in the blood, spleen, bronchia, mesenteric and retro-pharyngeal lymph nodes and Peyer's patches. Sample preparation is substantially as done for Ig response measurement of the ETEC IC vaccine.
  b) ELISA for IC-specific IgG and IgA: The ELISA procedure can be conducted according to substantially the same procedure as used for ELISA determination of IgG's and IgA's against the ETEC IC vaccine, with the difference that the microtiter plate wells are coated with Mab's specific to the IC's based on *C. albicans* Ribosomal Complex.
  c) Elispot assay for IC-specific IgG- and IgA secreting cells: IC-coated plates are prepared as above and the Elispot assay is also conducted as previously described.

8. Immune response following oral immunization with IC from *Candida albicans* in Chitosan-EDTA Bowman-Birk Inhibitor conjugate (CEBBI) tablets.
  a) Humoral immune response: blood drawn from pigs (immunized with either CEBBI-coated IC pellets [IC] or empty CEBBI-coated pellets [CEBBI]) on days 0, 8, 16, 23 and 31 post initiation of the experiment, can be analyzed for antigen-specific serum antibody titers. Results show that substantial increase of the antigen-specific IgA and IgG titers occurs in blood serum versus placebo. This is visible by day 8 and continues to increase on day 16 and day 23. Values measured on day 31 remain very high. In addition, one can observe that the CEBBI coated pellets in themselves do not induce specific immunity.
  b) The induction of antigen-specific secreted IgA's: Saliva samples can also be evaluated on days 0, 8, 16, 23 and 31 post initiation of the experiment. Results show that IgA levels in saliva samples behave similarly to serum IgA level, demonstrating strong mucosal immune induction by IC-CEBBI versus placebo.
  c) Localization and quantification of antigen-specific antibody-secreting cells (ASC): The number of IC-specific ASC (IgG and IgA) can be determined at days 0, 16, 23 and 31 post initiation of the experiment in blood, spleen, bronchia, mesenteric and retro-pharyngeal lymph nodes and Peyer's patches. Results show that (1) strong induction of both IgA and IgG ASC's is apparent on day 16 and day 23 in Peyer's Patches and RPLN, (2) IgA ASC's are also significant after 23 days in spleen, MLN and blood serum, (3) by day 31, specific IgA ASC's are abundant in both inductor and effector immune tissues, (4) by d 31, specific IgG ASC's remain present in high numbers in MLN, RPLN and PP.
  d) Inhibition of binding of *C. albicans* to human buccal epithelial cells by secreted IgA's of immunized pigs. Human buccal epithelial cells (HBEC) are suspended in a Hanks balanced salt solution containing 0.2% bovine serum albumin (BSA), 0.02% $Ca^{2+}$, and 0.02% $Mg^{2+}$ (Hanks/BSA) to a final concentration of $1.25\times10^5$ cells per ml. A virulent *C. albicans* strain that has undergone few passages on culture media, such as IPca1809, can be used for this binding assay. IPac1809 is inoculated in 10 ml of Yeast Nitrogen Base (Difco Laboratories, Mich. USA) containing 500 mM galactose and 50 μCi of [$^{14}$C] acetic acid (C.E.A. Saclay, France). After 48 h at 25° C. with constant agitation (180 rpm), the yeasts are harvested and washed 5 times with a phosphate-buffered saline (PBS) solution (10 mM phosphate in a 0.15 M NaCl solution [pH 7.2]). The yeast phase is then resuspended in Hanks/BSA, just before mixing with HBEC, to a concentration of $1\times10^8$ cells per ml and specific radioactivity of $1\times10^6$ to $1.25\times10^6$ cpm/$10^8$ cells). IgA's are purified and concentrated from pig saliva and feces applying standard sheep anti-swine IgA affinity chromatography, followed by an additional affinity chromatography using IC as ligand. To further purify the swine IgA's, the affinity column elute can be loaded onto a protein A Sepharose CL-4B column and washed extensively with PBS. The bound antibody is then eluted with 0.2 M acetate buffer (pH 3.5) containing 0.15 M NaCl, followed by neutralization. The antibody can subsequently be concentrated by ultrafiltration on preparatory scale Tangential Flow Filtration (TFF) membrane (MW cut-off 30 kDa; Millipore, USA) with 10 volumes of Hank's/BSA to a final concentration of 100 μg/ml (protein content of antibody preparations measured by Lowry method). The final antibody solution is sterilized by filtration through a 0.33 μm membrane and stored at 4° C. until used. 0.1 ml *C. albicans* IPCA1809 cells ($1\times10^8$/ml in Hanks/BSA) are mixed with one of 3 solutions: [1] 0.5 ml Hank's/BSA; [2] 0.5 ml IgA's from IC-CEBBI immunized pigs; [3] 0.5 ml IgA's from CEBBI inoculated pigs (no IC). 50.000 HBEC cells in 0.4 ml Hanks/BSA are subsequently separately mixed with above solutions [1] to [3] (respectively called HBEC 1, HBEC 2 and HBEC3) and incubated in 5 ml plastic tubes during 1 hour at 25° C. and rotated at 80 rpm. The suspensions are then passed through 12 μm-pore size polycarbonate filters (Nucleopore Corp., Ca, USA) by using a vacuum filtration system (Millipore SA, France). These filters retain epithelial cells with adherent *C. albicans* cells, whereas nonadherent *C. albicans* cells are washed through the filter. To remove unbound and co-adhesive yeast cells, the filters are then washed three times with 5 ml of Hanks/BSA, transferred in scintillation vials containing 1 ml of Hyamine hydroxide (Dupont, NEN Research Products, Mass. USA), and finally incubated for 1 h at 60° C. Counting is conducted after addition of 10 ml of Ultimagold scintillation cocktail (Packard Co., Ill. USA) in an LKB scintillation counter (type 1219 Rack-beta). All test samples are assayed in triplicate, and each assay is repeated 3 times. To eliminate background counts from *C. albicans* (CAB) alone, all experiments should include measurement of $^{14}$C on filters after passage of $1\times10^7$ yeast cells in 1 ml Hanks/BSA. The percentage of adhesion using respectively HBEC 2 and HBEC 3 is calculated as follows:

$$= 100 \times \left(\frac{\text{cpm}\,HBEC2 - \text{cpm}\,CAB}{\text{cpm}\,HBEC1 - \text{cpm}\,CAB}\right) \text{ and } =$$

$$100 \times \left(\frac{\text{cpm}\,HBEC3 - \text{cpm}\,CAB}{\text{cpm}\,HBEC1 - \text{cpm}\,CAB}\right)$$

Typical results (mean±standard deviation) are: HBEC 2=13.6%±5.4%

HBEC 3=56.5%±11.1%

The amount of *C. albicans* cells added relative to the amount of target BBEC cells is important as one may titrate the IgA's with an excess *C. albicans* cells. A person skilled in the art will know how to address this problem by experimenting with different IgA dilutions and different quantities of *C. albicans* cells. With abundant IgA's present, it can be observed that strong inhibition of adhesion of *C. albicans* to HBEC occurs in case the IgA's are derived from IC-CEBBI treated pigs. This does not occur with IgA's from pigs treated with the CEBBI delivery system alone.

Similar results are obtained when using cultured human umbilical vein endothelial cells from newborn babies (obtainable from la Clinique Maternité St-Jean, Toulouse, France), cultured human keratinocytes isolated from human foreskin (obtained from routine circumcisions at Purpan Pediatric Surgery Department, Toulouse, France), and cultured HeLa cells (from a human cervical carcinoma cell-line).

Taken together, the above findings illustrate that an Immunogenic Complex from *Candida albicans* in Chitosan-EDTA Bowman-Birk Inhibitor conjugate (IC-CEBBI) induces a strong and specific systemic and mucosal immune response in its host; in particular at effector sites where the pathogen is present (buccal and pharyngeal-intestinal tract). The delivery system in itself (CEBBI) does not have this effect. In addition, the produced secretory IgA's from subjects immunized with IC-CEBBI effectively bind pathogen cells hereby disabling adhesion of the pathogen to targeted human epithelial and endothelial cells. As adhesion of the pathogen to host cells (crucial step in disease establishment) is inhibited, said immunization enhances host defense against the pathogen.

EXAMPLE 3

Preparation, Administration and Evaluation of a Vaccine Against Periodontal Disease Based on Heterologous Immunogenic Complex Periodontitis is characterized by the presence of a complex interdependent micro-flora, including species such as *Treponema denticola, Actinobacillus actinomycetemcomitans, Campylobacter rectus* (formerly *Wolinella recta*), *Porphyromonas gingivalis* (formerly *Bacteroides gingivalis*). Here we describe a vaccine containing a Heterologous Immunogenic Complex consisting of Ribosomal Complex of *T. denticola, C. rectus* and *P. gingivalis* and as Adhesin, the Major Surface Protein (Msp) of *T. denticola*. Preparation of Immunogenic Complex from periodontal pathogens is best done from virulent, clinical isolates as they effectively contain and express the required surface antigens.

1. Growth of *Campylobacter rectus*: A virulent *C. rectus* strain from human periodontal pockets (obtainable from surgical dentistry practices) is used. In this example we refer to such a strain called IPcr3323. Cultures are maintained by bimonthly transfer on enriched trypticase soy agar as described by Syed SA., 1980, and grown for preparative purposes in Mycoplasma-formate-fumarate broth (mmf) as described by Gillespie and Holt, 1987 and with following specifications per liter. 21 g Mycoplasma broth base (BBL Microbiology Systems, MD, USA), 30 mM ammonium formate, 20 mM disodium fumarate and 40 mM N-2-hydroxyethylpiperazine-N'-2-ethanesulfonic acid (HEPES) buffer. Cultivation can be achieved in a Coy anaerobic chamber (Coy Laboratory Products, MI, USA) at 37° C. in an atmosphere of 85% nitrogen+10% hydrogen+5% carbon dioxide. Media are best pre-equilibrated under this atmosphere for 24 hours.
2. Growth of *Treponema denticola*: A virulent *T. denticola* strain from human periodontal pockets (obtainable from surgical dentistry practices) is used. In this example we refer to such a strain called IPtd2709. Cultures are grown in TP broth medium and maintained by weekly transfers. 1 L of TP broth contains 12.5 g of brain heart infusion medium (Difco Laboratories, Mich. US), 10 g or Trypticase (BBL Microbiology Systems, Md. US), 2.5 g of yeast extract (Difco), 0.5 g sodium thioglycolate (Difco), 1 g of L-cysteine hydrochloride (Sigma Chemical Co., Mo, US), 0.25 g of L-asparagine (Sigma), 2 g of glucose (Difco), 6 mg of thiamine pyrophosphate (Sigma), 0.01% [vol./vol.] isobuteric acid (Sigma), 0.01% [vol./vol.] isovaleric acid (Sigma), 0.01% [vol./vol.] valeric acid (Sigma), 2% [wt/vol.] sodium bicarbonate (Fisher), and 20 ml of heat-inactivated horse serum (GIBCO, Ontario, Can). Cultivation can be done in a Coy anaerobic chamber (Coy Laboratory Products) at 37° C. in an atmosphere of 85% nitrogen+10% hydrogen+5% carbon dioxide. Media are best pre-equilibrated under this atmosphere for 24 hours.
3. Growth of *Porphyromonas gingivalis*: A virulent *P. gingivalis* strain from human periodontal pockets (obtainable from surgical dentistry practices) is used. In this example we refer to such a strain called IPpg0202. Cultures can be grown under anaerobic conditions: 80% N2, 10% $CO_2$, and 10% $H_2$ in enriched brain/hart infusion broth (Difco), containing per liter, 37 g brain heart infusion, 5 g yeast extract (Difco), 1 g cysteine, 1 mg hemin and 1 mg vitamin $K_1$. Trypticase soy agar is included for maintenance on solid medium Media are best pre-equilibrated under this atmosphere for 24 hours.
4. Preparation of Ribosomal Complex from periodontal bacteria: Ribosomal Complex is prepared from mid-log phase cultures of *T. denticola, C. rectus* and *P. gingivalis* which have not undergone more than 6 subcultures and essentially as described earlier in this disclosure.
5. Production of antibodies against major *Treponema denticola* surface antigens.
a) Preparation of major surface antigens of *T. denticola*: Cultured *T. denticola* cells (see above) are harvested, washed and suspended in phosphate-buffered saline (PBS; 10 mM $Na_2HPO_4$, 150 mM NaCl, 2.5 mM KCL, 1.5 mM $KH_2PO_4$ [pH 7.2]), to and $OD_{600}$ of 0.2 ($5 \times 10^9$ cells per ml). Cell suspensions are subjected to mild sonification (six pulses of 15 sec. spaced 10 sec. apart at an output of 2 with a Sonifier Cell Disrupter 350 (Branson Sonic Power Co., Conn. USA), which primarily releases outer sheath material of the treponemes. Unbroken cells are removed by centrifugation (8000×g, 10 min.). The supernatant is centrifuged again at 16.000×g for 10 min. and the upper, lighter-colored area of the pellet is very carefully collected and suspended in PBS. SDS-polyacrylamide gel electrophoresis (PAGE) can be done using a Mini Protean II electrophoresis apparatus (Bio-Rad, Ca, USA) to estimate the enrichment for the Major Surface Protein (MSP) of *T. denticola*.
b) Production of antibodies against the major surface antigens of *T. denticola*: New Zealand White rabbits are immunized with approximately 0.5 mg of the preparation of major surface antigens of *T. denticola* in complete Freund's adjuvant. Subsequent intra-muscular injections without adjuvant can be performed after 1, 2,3,5 and 7 weeks. The rabbits are bled 1 week after the last injection. The specificity of the antiserum for MSP can be determined by ELISA, using alkaline phosphatase-conjugated goat anti-rabbit antibody (1:5000; Bethesda Research Laboratories, MD, USA). Immunoglobulins can be purified from immune serum by using standard protein A-Sepharose methods.
6. Cloning, expression in and purification from *Escherichia coli* of the msp gene, encoding the MSP protein of *Treponema denticola*. MSP is directly involved in the interaction between the spirochete and the gingival epithelium in periodontal diseases. MSP depolarizes epithelial cell membranes and binds to extracellular matrix components of epithelial cells. In addition to its Adhesin properties, MSP has been shown to have porin activity.

The objective of this experiment is to over-express the major surface protein (MSP) of *Treponema denticola* in *E. coli* because purification of MSP directly from *T. denticola* commonly results in contamination with other surface-associated components including lipo-polysaccharides, peptidoglycans and chymotrypsin-like surface protease.

a) Cloning of the msp gene: Preparative scale production of recombinant proteins from *E. coli* is well established. Chromosomal DNA of *T. denticola* can best be prepared from virulent, clinical isolates such as IPtd2709: DNA from a 1 l culture can be extracted as described by Silhavy et al., 1984, but to ensure complete and rapid cell lysis and inactivation of endogenous endonucleases, final SDS concentration is raised to 2% and incubation during lysis is 65° C. Chromosomal DNA is further purified by cesium chloride density gradient ultracentrifugation. Recombinant DNA methods for PCR based cloning are present in the literature and well known to a person skilled in the Art. The nucleotide sequence of the Msp gene can be obtained from GenBank under accession number U29399.

b) Expression of the MSP protein in *E. coli*: Once the full-length Msp gene has been cloned, subcloning in an expression plasmid vector is done. A vector such as for example pET17b (NOVAGEN) can be used. In this case DNA is transformed into *E. coli* BL21(DE3)/pLysS (NOVAGEN). Cloning restriction sites and enzymes are chosen such that the isopropyl-β-D-thiogalactopyranoside (IPTG)-inducible T7 promoter and the T7 signal peptide sequence are 5' and in frame with the full-length recombinant MSP protein (without its own transit peptide sequence). Freshly transformed cells are inoculated into LB broth containing carbenicillin (50 µ/ml) (Sigma, Mo, USA) and chloramphenicol (34 µ/ml) (Sigma) at 30° C. with shaking until an $OD_{600}$ of 0.4 is reached. IPTG (Sigma) from a 100 mM stock solution is added to a final concentration of 0.4 mM, and the culture is further incubated for 30 to 120 min. at 37° C. As MSP has porin activity, it appears to be toxic in *E. coli*. Consequently it is recommended to monitor OD carefully to evaluate the optimal time point for harvest.

c) Preparation and purification of MSP protein: The IPTG-induced *T. denticola* cells are centrifuged (23.000×g, 20 min.) and the cell pellets are resuspended at $5 \times 10^9$ cells $ml^{-1}$ in 55 mM $NaPO_4$ pH 7.2 buffer containing 250-500 U enzyme $ml^{-1}$ and protease inhibitors (1 mM EDTA, 0.2 phenylmethyl-sulphonyl fluoride (PMSF), 1 µm leupeptin and 1 µm pepstatin) and cells can be broken by French press cell disruption process at 17.000 lb/in². The unbroken whole cells and debris are removed as pellet after centrifugation at 3000×g, 20 min. The MSP protein in the supernatant can be separated from other proteins by 2 sequential purification steps: As first step, ion exchange chromatography can be used essentially as described earlier for the purification of ALA1 and HWP1 proteins but calibrations adapted for the properties of the MSP protein. As second step, Immuno-affinity purification can be applied to pooled samples, essentially as follows: Immunoglobulins raised against the major surface antigens of *T. denticola* are bound to protein A-Sepharose in the presence of 0.1 M borate (pH 9.0) and covalently coupled by using dimethyl suberimidate-2HCL (Pierce Chemical Co., Ill. USA). An appropriately sized column of the affinity matrix is washed and equilibrated with TSA buffer (10 MM Tris-Cl [pH 8.0 at 4° C.], 140 mM NaCl, 0.025% $NaN_3$). The pooled samples are passed over the column, which is subsequently washed at low pH (50 mM glycine [pH 2.5], 140 mM NaCl, 0.1% Triton X-100) and the purified MSP is eluted from the column at high pH (50 mM triethanolamine [pH 11.5], 140 mM NaCl, 0.1 Triton X-100) and neutralized with 0.2 volume of 1 M Tris-HCL (pH 6.7). Eluate fractions are analyzed by duplicate SDS-PAGE. For coupling of MSP to Ribosomal Complex, MSP was passed over a buffer exchange column (Bio-Rad Econo-Pac 10DG) equilibrated with phosphate buffer (0.01M, pH 7.0) containing 0.01M (PMB) and protein concentration is adapted to 20 mg/ml as described earlier in this disclosure.

7. Preparation of Heterologous Immunogenic Complex derived from periodontal bacteria. Ribosomal Complex (RC) prepared from *T. denticola, C. rectus* and *P. gingivalis* are separately calibrated to 20 mg/ml in phosphate buffer (0.01M, pH 7.0) containing 0.01M $MgCl_2$ (PMB), and mixed in equal volumes. The RC mixture is mixed with the MSP preparation produced in *E. coli* (also at 20 mg/ml PMB) in a ratio of 9 to 1 [w/w]. The mixture can be stored deep-frozen in aliquots (−80° C.).

8. Immunization of rats with the different components, individual and combined of the Heterologous Immunogenic Complex. 150 Harlan Sprague-Dawley rats are used in 5 groups of 30 rats and are exposed to following antigens and control:
1) Msp from *Treponema denticola* expressed in and prepared from *E. coli*.
2) Ribosomal Complex (RC) prepared from *T. denticola*.
3) A mixed RC prepared from *T. denticola, C. rectus* and *P. gingivalis*.
4) Heterologous Immunogenic Complex (HIC) consisting of RC from *T. denticola, C. rectus,* and *P. gingivalis* and Msp of *T. denticola* (the latter expressed in and purified from *E. coli*).
5) Phosphate buffer (PMB).

From arrival in the laboratory, the dams and pups are best kept in covered sterile cages in a laminar flow hood and given Diet MIT305 (containing 5% sucrose) and deionized water ad libitum until the pups are weaned (18 days old). The animals are then provided Diet MIT200 (containing 67% sucrose) ad libitum throughout the experiment (28-49 days old). Immunizations of each group of rats pups are done with the respective antigens and control on day 28, by intranasal administration (15 µg in 15 µl per nostril, done twice) by means of a pipettor with sterile disposable tips. Seven and fourteen days after the first administration (d35 and d42) the rats are given booster immunizations (10 µg in 15 µl per nostril, administered twice).

9. Preparation of IgA's & IgG's from respectively saliva and serum of immunized rats. On day 49, saliva and serum samples are taken from rats of each group: rats are anesthetized by intra-muscular injection with ketamine-xylazine (9:5 vol./vol.; 0.14 ml/100 g of body weight), and individual saliva samples (approximately 1 ml/animal) are collected with a capillary Pasteur pipette after pilocarpine stimulation over a 15-min interval. Pilocarpine is given intraperitonially between 3 and 5 min after anesthesia (50 µl Pilocarpine as 1 mg/ml in Dulbecco's phosphate-bufferedsaline [D-PBS {pH 7.3}: 2.7 mM KCl, 1.5 mM $KH_2PO_4$, 136 mM NaCl, 8.1 mM $NaHPO_4$]) The saliva samples are then centrifuged (800×g for 30 min, 4° C.) and snap-frozen in liquid $N_2$ and stored at −70° C. until assayed for IgA antibody activity against the respective antigens and control as described below. After the collection of saliva, all available blood can be collected by cardiac puncture, allowed to clot at room temperature for 1 h, and stored overnight at 4° C. Serum is separated from the clot by centrifugation (3500 g for 30 min, 4° C.) and stored at −20° C. until it assayed for IgG antibody activity by ELISA as described below.

10. ELISA for IC-specific IgG and IgA. The objective is to evaluate the specificity of salivary IgA's and serum IgG's, induced by the different antigens and control used for immunization of the 5 rat groups, against the respective antigenic components. 96-well microtiter plates are coated with following respective antigens at a total concentration of 100 µg/ml ELISA dilution buffer and incubated for 1 hour at 37° C. or 18 hours at 4° C.: Msp of T. denticola, RC of T. denticola, RC of C. Rectus, RC of P. gingivalis. Plates are washed three times with 350 µl of PBST (D-PBS containing 0.05% [vol/vol] Tween 20) per well. The remaining binding sites are blocked for 40 min. with 250 µl of PBS-Blotto (D-PBS containing 5% [wt/vol] nonfat dry milk) per well for 5 h at room temperature. Plates are washed 4 times with PBST before 75 µl of Rat saliva samples (for IgA counts) or rat sera (for IgG counts) in four two-fold dilutions in ELISA dilution buffer are added in duplicate to individual wells and plates are incubated overnight at 4° C. As controls, six twofold dilutions of the serum or saliva pool control are added to microtiter wells and treated identically. The plates are again washed 4 times with PBST, 75 µl of horseradish peroxidase-labeled goat anti-mouse IgG or IgA, both diluted 1:2000 in PBS-Blotto, are applied per well, and the plates are incubated for 90 min at room temperature. Plates are then washed 6 times with PBST, and color is developed at room temperature in the dark by adding 75 µl of a highly sensitive two-component tetramethylbenzidine substrate reagent which contains 1 mM 3,3',5,5'-tetramethylbenzidine and 3 mM $H_2O_2$ in 200 mM potassium cirate buffer (pH 4.0) per well. The reaction is terminated after 30 min by addition of 125 µl of 1 M sulfuric acid per well, and the plates can be read at 450 nm on a $E_{max}$ precision microtiter plate reader (Molecular Devices, Sunnydale, Calif., USA). A standard curve of antibody activity (in ELISA units [EU]) can be established by using a serum or saliva pool standard which was assigned a level of activity (in EU/ml), whereby 1 EU/ml equals the dilution of the standard giving an optical density reading of 0.1. The level of antibody activity (in EU/ml) in serum and saliva samples run simultaneously with the standard, can be determined by interpolation from the standard curve. Multi-parameter logistic algorithm (Softmax; Molecular Devices Crop, USA) can be used for analysis. The significance of differences of the means of antibody levels can be determined by analysis of variance with Statview II software (Abacus Concepts, Ca, USA).

11. Induction and specificity of salivary IgA's and serum IgG's of rats immunized respectively with the Heterologous Immunogenic Complex (HIC) and parts thereof. Results of experiments as described above show that (1) anti-MSP salivary IgA and anti-MSP serum IgG responses to MSP antigen are significant but weak, (2) that RC of T.d. has cross-reactivity to MSP of T.d., (3) that anti-MSP responses induced by RC of T. denticola (alone or in conjunction with RC of other microbes) is stronger than anti-MSP response to MSP, (4) that HIC specific IgA and IgG titers against MSP antigen are higher than those of antibodies induced by MSP alone and higher than those induced by RC of T.d. and those induced by the mixed RC of T.d. plus P.g. plus C.r., (5) that RC of T.d. has cross-reactivity against RC of P.g. and RC of C.r., (6) that RC's either alone, combined or coupled with MSP, induce salivary IgA and IgG responses to the corresponding RC antigens.

12. Inhibition assay of binding of respectively T. denticola, C. rectus and P. gingivalis to human buccal epithelial cells by secreted IgA's induced by HIC immunization. Gingival pocket epithelium can be surgically prepared from patients with periodontal infections. Tissue samples are thoroughly rinsed with sterile saline solution and placed in Dulbecco's Modified Eagle's Medium (DMEM) (Gibco, Life Technologies Ltd, UK), supplemented with 100 λ penicillin and 100 µg/ml streptomycin, for transport to the laboratory (samples from 3 female patients, diagnosed with chronic adult Periodontitis are used in this example). Establishment of confluent monolayers of epithelial cells can be done according to Papaioannou W. et al., 1999.

IgA's from bulked saliva samples (±15 ml) of rats of group 1 to 5 are purified and concentrated essentially as described in Example 2 except that final antibody solutions do not need to be quantified and can be resuspended in 1 ml keratinocyte-serum free medium (KSFM). Virulent strains of clinical periodontal diseased patients are best used. In this example: T. denticola strain IPtd2709, P. gingivalis strain IPpg0202 and C. rectus strain IPcr3323 are inoculated on appropriate media (see earlier), supplemented with 0.8% (w/vol.) agar to increase the hardness of the agar plates and are incubated for 48 hours at appropriate temperature and atmospheric conditions (see earlier). Strains should best not have undergone more than 6 subcultures prior to the experiment. Bacteria are subsequently collected, washed 3× with a sterile saline solution and resuspended in KSFM at concentrations adjusted to $1 \times 10^8$/ml (optical density measurement based on a previously calculated optical density/bacterial concentration gradient curve).

Subsequently 0.5 ml of each strain ($5 \times 10^7$ cells) is mixed respectively with 0.2 ml of IgA samples derived from rats of Group 1 to 5 and added to each well, containing a mono-layer of human epithelial cells in 37° C. air with 5% $CO_2$ under continuous shaking for 90 min. After incubation of the wells with the bacteria for 90 minutes, they are washed 4× with sterile saline solution. The epithelial cells and their adhering bacteria from the plastic wells are trypsinized with 0.5 ml of 0.25% trypsin/EDTA (Gibco) for 15 min. Afterwards, 0.5 ml saline solution is added to each well, raising total volume to 1 ml. Serial dilutions are prepared after thorough pipetting and vortexing the initial solution. The dilutions are plated in duplicate onto appropriate bacterial media (see earlier) supplemented with agar. For each strain, serial dilutions of the initial concentration are also plated to control the number of bacteria added to each well. After 5 days of anaerobic growth (according to specifications given earlier), the total number of Colony Forming Units (CFU) per well is counted.

An equivalent set of epithelial cells can also be cultivated in plastic wells containing 12 mm cover slips for direct microscopy and they are treated identically in parallel. After the 4× wash with sterile saline solution, the epithelial cells and adhering bacteria are fixed with 0.5 ml of 0.1% gluteraldehyde. The fixative is removed and the cells are washed 3× with sterile saline solution. Subsequently, 0.5 ml of a saline solution, containing a fluorescent stain (Live/dead Baclight bacterial viability kit, Molecular Probes Inc. Or, USA) at 3 µl/ml, is added to each well. The wells with the stains are left in the dark at room temperature for 15 min. The stain is removed and the cover slips are washed twice. They are removed from the wells and placed on microscope slides for analysis with a fluorescent microscope with dual fluorescent filter (fluorescein/Texas red) at magnification 25×. For each monolayer, the number of living adhering bacteria on 10 representative "live" epithelial cells are counted for 3 different fields under 1000× magnification. Both experiments are best conducted in multiple (in triple). The differences between the mean values can be appreciated using a Student T-test (p=0.05).

13. Inhibition of binding of respectively *T. denticola, C. rectus* and *P. gingivalis* to human buccal epithelial cells by secreted IgA's induced by cHIC immunization.

The results show that (1) IgA's from rats immunized with MSP of *T. denticola* and IgA's from mock-immunized rats (PMB buffer), do not significantly interfere with adherence of any of the three tested periodontopathogens to human epithelial cells, (2) IgA's from rats immunized with RC of *T. denticola* as well as IgA's from RC of all 3 bacteria significantly inhibit binding of *T. denticola* to human epithelial cells, (3) IgA's from rats immunized with RC of *T. denticola* do not significantly inhibit binding of *P. gingivalis* nor of *C. rectus* to Human epithelial cells (4) observations (2) and (3) indicate that these RC's do not induce significant cross-reactive IgA's to the intact bacteria of the other species, (5) IgA's from rats immunized with HIC significantly inhibit binding of all 3 species of periodontopathogens with human epithelial cells, (6) IgA's from rats immunized with HIC more strongly inhibit binding of *T. denticola* to human epithelial cells than either the Adhesin Msp, the RC of *T. denticola* or RC of the 3 periodontal pathogens, (7) both binding assay methods presented show compatible results.

Taken together the above immunization experiments and IgA binding experiments demonstrate that Heterologous Immunogenic Complex can induce a strong and specific humoral and mucosal immune response in its host and that the induced secretory IgA's effectively inhibit binding of pathogen, cells of multiple species to target human epithelial cells. The results also illustrate that the Immunogenic Complex is more immunogenic and that resulting antibodies are substantially more effective in binding target Microbes and interfering with their invasion process of host cells, than its components, the Ribosomal Complex or Adhesin alone.

EXAMPLE 4

Vaccination of Rats Against Vaginal Candidiasis with Immunogenic Complex from *Candida albicans* in Chitosan-EDTA Bowman-Birk Inhibitor Conjugate (CEBBI) Pellets In this example we illustrate that the Immunogenic Complex (IC) consisting of Ribosomal Complex (RC) of *C. albicans* and the Adhesins ALA1 and HWP1, contained in mini-pellets consisting of gelatin and Chitosan-EDTA Bowman-Birk Inhibitor conjugate (CEBBI), can protect against vaginal candidiasis.

1. Preparation IC in gelatin-CEBBI mini-pellets. IC can be prepared as described in Example 2 but to the final formulation, a 10-fold excess (wt/wt) of gelatin is added. Pellets containing either IC or no IC (controls) can be formulated in 2 mg gelatin-CEBBI mini-pellets and stored at 4° C.
2. Immunization of rats against vaginal candidiasis. 30 ovariectomized female Wistar rats (Charles River Calco, Va, Italy), weighing approximately 100 g, are used. From arrival in the laboratory, they are kept in covered sterile cages in a laminar flow hood and maintained in pseudoestrus by injection of estradiol benzoate (0.5 mg in 0.1 ml subcutaneously (Benzatron, Samil, Italy) every two days. 1 day after arrival in the laboratory the rats are divided in 3 groups of 10 rats. Rats in Group 1 are made to swallow one IC-gelatin-CEBBI pellet per day, for 3 days, with one repetition after 7 days and 14 days. Rats in Group 2 receive one gelatin-CEBBI pellet (control) per day, for 3 days, with one repetition after 7 days and 14 days. Rats in Group 3 receive nothing. 18 days after the first estradiol dose, the 3 Groups are inoculated intra-vaginally with $10^7$ yeast cells of *C. albicans* strain 3153, wild-type for aspartyl proteinase secretion (Ross I. K. et al., 1990) in 0.1 ml of saline solution, administered to each animal through a syringe equipped with a multipurpose calibrated tip (Combitip, PBI, France). Vaginal fluid is taken from each animal every 2 days for 10 days with a calibrated (1 µl) plastic loop (Dispoinoic, PBI, France), by insertion and removal from the vagina. Fluids can be used to measure vaginal colonization. To this purpose the content of each loop is vigorously suspended in 0.1 ml of PBS and aliquots are streaked in triplicate on Sabouraud-dextrose agar with chloramphenicol (20 µl ml$^{-1}$) to calculate the colony-forming units (CFU ml$^{-1}$) after incubation of the plates at 30° C. for 48 h. At intervals during the experimental infection, it is best to evaluate colony development on agar for species identification in order not to introduce counting errors.

Response of rats immunized with IC-gelatin-CEBBI minipellets to vaginal infection with *Candida albicans*. Immune response can be measured by evaluation of the relative proliferation of *C. albicans* strain 3153 in the vagina's of the 3 groups of rats, respectively immunized with IC-gelatin-CEBBI pellets (Group 1), with gelatin-CEBBI pellets (Group 2) or not immunized (Group 3). Data submitted to Mann-Whitney test with P<0.01 show statistically significant results that can be summarized as follows: (1) rats immunized with Immunogenic Complex, derived from *C. albicans* Ribosomal Complex and Adhesins ALA1 and HWP1, formulated in gelatin-CEBBI pellets, rapidly reduce the number of viable *C. albicans* cells in the vagina when compared to mock immunized or not immunized rats, (2) no significant differences are seen in the number of viable *C. albicans* cells over the time course of the experiment between mock immunized rats (Group 2) and non-immunized rats (Group 3), indicating that the immune response against *C. albicans* in Group 1 is due to the presence of Immunogenic Complex (IC) of *C. albicans* and not due to the gelatin-CEBBI formulation, (3) IC prepared from one *C. albicans* strain (IPca1809) can cross-protection against another *C. albicans* strain (3153), (4) Immune induction by IC via the oral-gastrointestinal tract can induce a mucosal immune response in other effector tissues (vaginal epidermal surface).

EXAMPLE 5

Preparation, Administration and Evaluation of a Vaccine Against Influenza A Virus, Strain H5N1, Based on Immunogenic Complex Influenza A virus is a highly infectious respiratory pathogen of humans, birds and pigs. Given the fact that Influenza strains from birds, pigs and humans cross-infect and potentially recombine, new pandemics can be foreseen and require the development of effective, safe and easy to administer prophylactic vaccins. This example illustrates the use of Immunogenic Complex as a mucosal vaccine against the H1N1 influenza virus (A/Swine/Indiana/1726/88).

1. Preparation of Ribosomal Complex (RC): Non-dissociated ribosomes can be prepared from Rnase-minus *Escherichia coli* strain MRE600 as described earlier. The preparations are adjusted to 20 mg/ml and maintained at −70° C. until used. The MRE600 strain can be obtained from the ATCC (Rockville, Md., USA), but other *E. coli* strains can also be used.

2. Isolation of influenza hemagglutinin (HA) glycoprotein: The H1N1 (A/Swine/Indiana/1726/88) influenza virus can be cultivated in 10-day old embryonated hen's eggs. The virus can be isolated according to standard methods, such as described by Sheerar, M. G., B. Easterday and V. S. Hinshaw. 1989, Antigenic conservation of H1N1 swine influenza viruses. J. Gen. Virol. 70: 3297-3303, except that the allantoic fluid is centrifuged at 8000-×g prior to purification on 30% to 60% sucrose gradients at 24000 rpm in a SW 28 rotor (Beckman). All manipulations with live virus need to be done under biosafety level 2 (or level 3) containment. Virus, stored at −70° C., is used to purify HA according to standard methods, such as described by Brand C. M. and J. J. Skehel, 1972. The protein concentration can subsequently be measured and concentration of aliquots can be set at 20 mg/ml prior to storage at −70° C. until used. Obviously other influenza serotypes can also be used.

3. Preparation of Immunogenic Complex (IC) consisting of Ribosomal Complex (RC) and hemagglutinin (HA) coupled by means of biotin-avidin bridges:

a) Biotinylation: RC and HA fractions are thawed on ice and separately dialyzed against 0.1 M $NaHCO_3$, 6 mM $MgCl_2$ and 10 mM KCl, pH 8.3. Final concentrations can be adjusted to 2 mg/ml. Sulfosuccinimidyl 6-(biotinamido) hexanoate (Pierce, Rockford, Ill., USA) is dissolved at 1 mg/ml in dimethyl sulfoxide. A 15-fold molar excess of the biotin ester is added to the separate RC and HA fractions (0.12 ml of Biotin ester per ml of protein). The reaction is allowed to proceed for 2 h at room temperature after which unreacted reagent is removed by dialysis against phosphate-buffered saline (PBS), pH 7.4, supplemented with 6 mM $MgCl_2$ and 10 mM KCl.

b) Avidin coupling to biotinylated RC: At neutral pH, avidin exists as a tetramer with four potential biotin-binding sites. By incubating biotinylated RC (molecular weight approximately 2500 Kd) with approximately five- to tenfold molar excess of avidin, RC particles saturated with avidin are created. The RC-avidin particles can be separated from the excess free avidin by gel filtration chromatography or centrifugation through a 40% sucrose cushion. In the latter case, the avidin remains in the gradient while the RC-avidin particles are pelleted. The sucrose gradient is supplemented with 6 mM $MgCl_2$ and 10 mM KCl. An avidin-binding dye, 4-hydroxyazobenzene-2'-carboxylic acid (HABA) can be used in a colorimetric assay to confirm the Biotinylation of the RC and the HA and estimate the quantity of biotin-binding sites on the RC-avidin particles.

c) Coupling of biotinylated HA to the RC-Avidin particles: The purified RC-avidin particles, resuspended in PBS, pH 7.4 supplemented with 6 mM $MgCl_2$, 10 mM KCl. possess free biotin-binding sites through which subsequently biotinylated HA, added in five- to tenfold molar excess, can bind to form RC—avidin—HA Immunogenic Complexes. These Immunogenic Complexes (IC) can be separated from the excess biotinylated HA as described above (gel filtration or sucrose gradient centrifugation).

4. Procedure to vaccinate pigs with IC consisting of conjugated RC—avidin—HA Immunogenic Complexes.

d) Pigs: 35 H1N1influenza virus-sero-negative pigs (Belgian Landrace×Piétrain), 9 weeks of age, can be used.

e) Nasal and oral administration of IC: A first group of 10 pigs is administered respectively 5 mg/pig/day of IC in 10 ml physiological solution+6 mM $MgCl_2$, 10 mM KCl, administered with a plastic needle-less syringe to the distal sublingual cavity The same animals also receive 5 mg/pig/day of IC in 10 ml physiological solution supplemented with 6 mM $MgCl_2$, 10 mM KCl instilled intranasally. A control group of 10 pigs receives avidin-bound biotinylated RC without HA suspended in physiological solutions+6 mM $MgCl_2$, 10 mM KCl in the same doses and locations. The IC and the placebo are respectively administered for 2 successive days and once again on day 15 to the 2 sets of 10 pigs. Blood samples and nasal swabs are taken from each pig on days 7, 14, 21, 28 and 35 post initiation of the immunization program. Nasal swabs and blood samples are also taken from 5 pigs at day 0. These animals are not further used in the experiment (day zero control).

f) Virus challenge: Seven pigs of both the experimental and the placebo group are challenged on day 22 by intranasal instillation of $3\times10^4$ or $3\times10^6$ 50% egg infective doses ($EID_{50}S$) of A/Swine/Indiana/1726/88 virus. Challenged pigs are monitored daily for clinical signs and compared to the six non-challenged pigs. Nasal swabs are collected from all challenged pigs on days 23, 26, 30 and 35. Virus titers are can be determined by limiting-dilution assays in embryonated hens' eggs. As negative control, nasal swabs from non-challenged pigs, on each time-point, can be used to inoculate embryonated hens' eggs. However, prior to inoculation, it is recommended to filter sterilize the samples in order to eliminate microbial contamination.

5. Procedure to evaluate mucosal vaccination efficacy of the Immunogenic Complex (IC) consisting of Ribosomal Complex (RC) and hemagglutinin (HA), coupled by means of biotin-avidin bridges:

a) Sample preparation for serum IgA and IgG response measurement: HA-specific IgG antibodies can be determined in the blood and HA-specific IgA's can be measured in the nasal swabs: serum is incubated for 18 hours incubation at room temperature. Nasal swabs are stored at 4° C. Subsequently Serum samples and nasal swabs are inactivated at 56° C. for 30 minutes, diluted with 1 volume of D-PBS (Dulbecco's phosphate-buffered saline [pH 7.3]:2.7 mM KCl, 1.5 mM $KH_2PO_4$, 136 mM NaCl, 8.1 mM $NaHPO_4$) and incubated at room temperature for 30 min. The suspension is centrifuged at 5500-×g for 10 min and the supernatant is further diluted in PBST (D-PBS supplemented with 0.05% [vol/vol] Tween-20), yielding a final serum-, respectively swab dilution of 1/10.

b) ELISA for IC-specific IgG and IgA: Micro titer plates are coated with 75 µl of HA (5 µg/ml) in 10 mM sodium phosphate buffer (pH 7.0) −10 mM NaCl per well overnight at 4° C. Plates are washed three times with 350 µl of PBST per well. Non-specific binding sites are blocked with 250 µl of PBS-Blotto (D-PBS supplemented with 5% [wt/vol] nonfat dry milk) per well for 5 h at room temperature. Plates are washed four times with PBST before 75 µl of serially diluted sera, nasal washes or anti HA-antibody standard in PBS-Blotto are applied per well, and the plates are incubated overnight at 4° C.

The plates are subsequently again washed four times with PBST, 75 µl of horseradish peroxidase-labeled goat anti-swine IgG or IgA, both diluted 1:2000 in PBS-Blotto, is applied per well, and the plates are incubated for 90 min at room temperature. Plates are again washed six times with PBST, and color can be developed at room temperature in the dark by adding 75 µl of a highly sensitive two-component tetra-methylbenzidine substrate reagent which contains 1 mM 3,3',5,5'-tetramethylbenzidine and 3 mM $H_2O_2$ in 200 mM potassium citrate buffer (pH 4.0) per well. The reaction is terminated after 30 min by addition of 125 µl of 1 M sulfuric acid per well, and the plates can be read at 450 nm on an $E_{max}$ precision micro titer plate reader (Molecular Devices, Sunnydale, Calif., USA). Specific antibody responses are expressed as endpoint titers, being the reciprocal of the highest dilution that gives a reading above the cutoff. The cutoff is defined as the upper limit of a 99.5% confidence interval above the mean control level and can be calculated by t statistics; e.g. for the 10 mock-immunized control animals and a 99.5% confidence interval, the cutoff is calculated as the mean$_{controls}$+5.0×SD$_{controls}$ where SD is the standard deviation. Titers are best transformed logarithmically [log (titer +1)] for calculation of group means and standard errors of the means (SEM) or used directly for correlation analysis.

6. Immune response following oral immunization with IC consisting of RC and influenza HA, coupled by means of biotin-avidin bridges:
a) Humoral immune response: The humoral immune response after the nasal instillation of IC on day 0 and of virus challenge on day 22 can be evaluated by determining the HA antigen-specific serum antibody titer on days 0, 7, 14, 21, and 35 post initiation of the experiment. A substantial increase of the hemagglutinin-specific IgG response versus controls can already be noted on day 7, which continues to increase on days 14, 21 and 28 after which it plateaus (no significant change on day 35 versus day 28).
b) Mucosal immune response: The secretion of HA-specific IgA's can be evaluated on samples collected on the same days as the blood samples. IgA's titers follow a similar pattern of induction pattern, as the humoral IgG's, although the final titers measured remain significantly lower than the IgG titers. This is likely due to the concentration of secreted IgA's in nasal swabs versus IgG's in blood. HA-specific responses against avidin-bound biotinylated RC's are not induced.

The results show that (1) the Immunogenic Complex (IC) consisting of Ribosomal Complex (RC) and influenza hemagglutinin (HA), coupled by means of biotin-avidin bridges induces strong humoral IgG and mucosal IgA responses in immunized pigs and (2) avidin-bound biotinylated RC's alone do not induce specific immune reactions against HA.

7. Immunity of vaccinated pigs following nasal instillation with IC consisting of biotin-avidin coupled RC and HA: The pigs infected with influenza A strain (H1N1) on day 22 can be analyzed for (1) clinical symptoms (fever), (2) physical activity versus the pig group vaccinated with avidin-bound biotinylated RC without HA and versus non-infected controls and (3) virus titers as determined by limiting-dilution assays in embryonated hens' eggs of microbially aseptic filtered nasal swab preparations.

Results show that (1) IC vaccinated pigs do not develop fever, contrary to control group (2) IC vaccinated pigs remain physically active (minutes in motion per hour) while sick pigs of the mock-immunized challenged group tend to stagnate or lie down, (3) IC vaccinated pigs have viral counts in their nasal swabs that are significantly lower than those of pigs that are mock-vaccinated with avidin-bound biotinylated RC's.

Jointly, the above illustrates that immunization of pigs against Influenza A virus with IC consisting of biotin-avidin coupled RC and HA is effective in inducing a strong, specific and protective humoral and mucosal immune response against Influenza A virus.

References

Brand C. M. and J. J. Skehel, Crystalline antigen from influenza virus envelope. Nature New Biology, 1972, 238: 145-147.

Cox E., Schrauwen E., Cools V., and Houvenaghel A., Experimental induction of diarrhea in newly-weaned pigs. J. Veterinary Med., 1991, 38: 418-426.

Externest D., B. Meckelein, M. A. Schmidt and A. Frey, Correlations between antibody immune responses at different mucosal effector sites are controlled by antigen type and dosage. Infect. Immun. 2000, 68: 3830-3839.

Gaur N. K., Klotz S. A., Henderson R. L., Over-expression of the *Candida albicans* ALA 1 gene in *Saccharomyces cerevisiae*. Results in aggregation following attachment of yeast cells to extracellular matrix proteins, adherence properties similar to those of *Candida albicans*. Infect. Immun. 1999, 67: 6040-6047.

Gietz R. D. and Schiestl R. H., Transforming yeast with DNA. Methods Mol. Cell. Biol., 1995, 5: 255-269.

Gregory R. L., Michalek S. M., Shechmeister I. L., and McGhee J. R., Effective immunity to dental caries: protection of gnotobiotic rats by local immunization with a ribosomal preparation of *Streptococcus mutans.* 1983, Microbiol. Immunol., 27: 797-800.

Hoffman A. R. and Winston F., A ten-minute DNA preparation from yeast efficiently releases autonomous plasmids for transformation of *Escherichia coli*. Gene 1987, 57: 267-272.

Jacobs, A. A. C., and de Graaf, F. K. Production of K88, K99 and F4 fibrillae in relation to growth phase, and a rapid procedure for adhesin purification. FEMS Microbiology Letters, 1985, 26,15-19.

Michalek S. M., and McGhee J. R., Effective immunity to dental caries: passive transfer to rats of antibodies to *Streptococcus mutans* elicits protection. 1977, Infect. Immun. 17: 644-650.

Papaioannou W., van Steenberghe D., Cassiman J -J., Van Eldere J., Quirynen M., Comparison of fluorescence microscopy and culture assays to quantitate adhesion of *Porphyromonas gingivalis* to Mono- and Multi-layered pocket epithelium cultures. J. Periodontol. 1999, 70: 618-625.

Youmans A. S., and Youmans G. P., Immunogenic activity of a ribosomal fraction obtained from *Mycobacterium tuberculosis.* 1965, J. Bacteriol. 89, 1291-1298.

Yusupov M. M. and A. S. Spirin. Hot tritium bombardment technique for ribosome surface topography. Methods in Enzymology, 1988, 164: 426-439.

Ross I. K., De Bemardis F., Emerson G. W., Cassone A., Sullivan P. A., The Secreted aspartate proteinase of *Candida albicans*: physiology of secretion and virulence of a proteinase-deficient mutant. J. Gen. Microbiol. 1990, 136: 687-694.

Sheerar, M. G., B. Easterday and V. S. Hinshaw. 1989, Antigenic conservation of H1N1 swine influenza viruses. J. Gen. Virol. 70: 3297-3303.

Silhavy T. J., Berman M. J., and Enquist, L. W., Experiments with gene fusions. Cold Spring Harbor Laboratory, Cold Spring Harbor, N.Y., 1984.

Staehelin T., D. Maglott and R. E. Monro. Cold Spring Harbor Symp. Quant. Biol. 1969,34:39.

The invention claimed is:

1. An immunogenic complex comprising:

(a) at least one ribosomal complex; and (b) at least one adhesin of a microbe; or (c) at least one viral antigen, wherein the ribosomal complex comprises the large and small ribosomal subunits, corresponding to 50S and 30S subunits in bacteria and 60S and 40S subunits in eucaryotes which subunits are particulate in nature, carry on their surface minor fractions of the microbial cellular membrane or cell wall components and contain large double stranded rRNA's corresponding to 16S and 23S in bacteria, and 18S and 28S in eukaryotic cytosol;

wherein the ribosomal complex retain integrity to preserve the double-stranded nature of the large r-RNA's contained in said ribosomal subunits; and wherein the immunogenic complex leads to the production of high levels of IgG antibodies.

2. The immunogenic complex of claim 1, wherein said adhesin is any protein embedded in or on the surface of any microbe, wherein said protein is involved in the interaction between the microbe and a host cell.

3. The immunogenic complex of claim 2, wherein said adhesin induces an antibody response to said protein.

4. The immunogenic complex of claim 2, wherein said host cell is a eukaryotic cell from a vertebrate animal.

5. The immunogenic complex of claim 4, wherein said host cell is selected from the group of absorptive enterocytes, M-cells, dendritic cells, macrophages, erythrocytes, fibroblasts and epithelial cells.

6. The immunogenic complex of claim 3, wherein said adhesin binds to extra-cellular matrix components that are embedded in said host cell.

7. The immunogenic complex of claim 6, wherein said extracellular matrix components are selected from the group consisting of fibronectin, laminin, collagen, fibrogen, vitronectin or heparin sulfate and analogues, and homologues thereof.

8. The immunogenic complex of claim 2, wherein said microbe is a fungus.

9. The immunogenic complex of claim 2, wherein said adhesin is a protein included in colonization factor antigens present in fungal hyphae.

10. The immunogenic complex of claim 1 comprising:
(a) a ribosomal complex; and
(b) an adhesin,
wherein said ribosomal complex and said adhesin originate from multiple microbes species, wherein said microbe species is any species selected from the group consisting of bacteria, fungi and protozoae.

11. The immunogenic complex of claim 1 comprising:
(a) a ribosomal complex; and
(b) an adhesin,
wherein said ribosomal complex and said adhesin originate from different or multiple microbes species, wherein from one or more species of said microbes,
(1) only said ribosomal complex, but not said adhesin;
(2) or only said adhesin and not said ribosomal complex, is included.

12. The immunogenic complex of claim 1, wherein said ribosomal complex and/or said adhesin is from *Candida albicans*.

13. The immunogenic complex of claim 1, wherein, that is a bacterio-viral complex, wherein said viral antigen originates from influenza virus.

14. The immunogenic complex of claim 1 comprising:
(a) a ribosomal complex; and
(b) an adhesin; or
(c) a viral antigen,
wherein said ribosomal complex: said adhesin is present in a weight ratio of 1:20 and 20 to 1, or said ribosomal complex:said viral antigen is present in a weight ratio of 1:20 and 20 to 1.

15. The immunogenic complex of claim 1, wherein said ribosomal complex and said adhesin or said viral antigen are incorporated into a carrier, consisting of polymeric matrices.

16. The immunogenic complex of claim 15, wherein said polymeric matrices comprises chitosan-EDTA Bowman-Birk Inhibitor conjugate.

17. The immunogenic complex of claim 1, wherein said ribosomal complex and said adhesin or said viral antigen are incorporated in microparticles.

18. The immunogenic complex of claim 17, wherein said micro-particles are coated with poly[dl-lactide-co-glycolide] (PLG).

19. The immunogenic complex of claim 1 comprising:
(a) a ribosomal complex; and
(b) an adhesin; or
(c) a viral antigen,
wherein (a), and (b), or (a) and (c) are non-covalently bound to each other by ionic interactions.

20. The immunogenic complex of claim 1 comprising:
(a) a ribosomal complex; and
(b) an adhesin; or
(c) a viral antigen,
wherein (a), and (b), or (a) and (c) are covalently coupled.

21. The immunogenic complex of claim 20, wherein said covalent coupling is chemically achieved using N-hydroxysuccinimidyl esters.

22. The immunogenic complex of claim 20, wherein said covalent coupling is chemically achieved using 1-(3-dimethylaminopropyl)-3-ethylcarbodiimide (EDC).

23. The immunogenic complex of claim 20, wherein said covalent coupling is chemically achieved using bis-imido esters.

24. The immunogenic complex of claim 20, wherein said covalent coupling is chemically achieved using glutaraldehyde.

25. A pharmaceutical composition comprising the immunogenic complex of claim 1, and a pharmaceutically acceptable carrier.

26. The pharmaceutical composition of claim 25, which is a vaccine.

27. The pharmaceutical composition of claim 26, which said vaccine is against a microbe.

28. The pharmaceutical composition of claim 26, wherein said vaccine is effective for preventing *Candida* infection, wherein the ribosomal complex is derived from *Candida albicans* and includes as an adhesin, ALA1 of said *C. albicans* or a protein structurally similar to, or any polypeptide derived from said ALA1, or corresponding to part of the ALA1 gene product, which can still induce an antibody response to said ALA1.

29. The pharmaceutical composition of claim 27, wherein said pharmaceutical is effective for preventing *Candida* infection, wherein the ribosomal complex is derived from *Candida albicans* and includes as an adhesin, the HWP1 protein of said *C. albicans* or a protein structurally similar to, or any polypeptide derived from said HWP1, or corresponding to part of the ALA1 gene product, which can still induce an antibody response to said HWP1.

30. The pharmaceutical composition of claim 25, that is effective for preventing infectious diseases in humans or in animals.

31. The pharmaceutical composition of claim 30, wherein said pharmaceutical if effective for preventing *Candida* infection.

32. A method of making the immunogenic complex of claim 1 comprising combining a ribosomal complex with an adhesin of one or multiples microbes.

33. The method of claim 32, wherein said ribosomal complex and said adhesin are incorporated into a carrier, comprising polymeric matrices that contain chitosan-EDTA Bowman-Birk Inhibitor conjugate.

34. The method of claim 32, wherein said ribosomal complex and the said adhesin are encapsulated in microparticles that contain carboxymethylethylcellulose-coated poly[di-lactide-co-glycolide] (PLG).

35. The method of claim 32, wherein said ribosomal complex and said adhesin are non-covalently bound to each other by ionic interactions.

36. The method of claim 32, wherein said ribosomal complex and said adhesin are covalently coupled to each other.

37. The method of claim 36, wherein said covalent coupling is achieved using N-hydroxysuccinimidyl esters.

38. The method of claim 36, wherein said covalent coupling is achieved using 1-(3-dimethylaminopropyl)-3-ethyl-carbodiimide (EDC).

39. The method of claim 36, wherein said covalent coupling is achieved using bis-imido esters.

40. The method of claim 39, wherein glutaraldehyde is used to achieve said bis-imido ester bond.

41. A method of making of a pharmaceutical composition comprising combining the immunogenic complex of claim 24 with a pharmaceutically acceptable carrier, diluent or other excipient.

42. The immunogenic complex of claim 4, wherein said vertebrate is selected from the group consisting of aves, pisces, mammalian, and humans.

* * * * *

UNITED STATES PATENT AND TRADEMARK OFFICE
CERTIFICATE OF CORRECTION

PATENT NO.       : 7,651,842 B2                                  Page 1 of 1
APPLICATION NO.  : 10/250664
DATED            : January 26, 2010
INVENTOR(S)      : Benedikt Timmerman It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1183 days.

Signed and Sealed this

Twenty-third Day of November, 2010

David J. Kappos
*Director of the United States Patent and Trademark Office*